(12) United States Patent
Grassauer et al.

(10) Patent No.: US 10,342,820 B2
(45) Date of Patent: *Jul. 9, 2019

(54) ANTIVIRAL COMPOSITION COMPRISING A SULFATED POLYSACCHARIDE

(75) Inventors: Andreas Grassauer, Vienna (AT); Eva Prieschl-Grassauer, Vienna (AT)

(73) Assignee: MARINOMED BIOTECH AG, Vienna (AT)

( * ) Notice: Subject to any disclaimer, the term of this patent is extended or adjusted under 35 U.S.C. 154(b) by 107 days.

This patent is subject to a terminal disclaimer.

(21) Appl. No.: 13/483,716

(22) Filed: May 30, 2012

(65) Prior Publication Data

US 2012/0237572 A1    Sep. 20, 2012

Related U.S. Application Data

(63) Continuation of application No. 12/673,145, filed as application No. PCT/EP2008/006910 on Aug. 22, 2008, now abandoned.

(60) Provisional application No. 60/935,668, filed on Aug. 24, 2007.

(51) Int. Cl.
*A61K 31/737* (2006.01)
*A61K 31/731* (2006.01)

(52) U.S. Cl.
CPC .......... *A61K 31/731* (2013.01); *A61K 31/737* (2013.01)

(58) Field of Classification Search
CPC .............................. A61K 31/737; A61K 31/731
See application file for complete search history.

(56) References Cited

U.S. PATENT DOCUMENTS

| 4,783,446 A | 11/1988 | Neushul |
| 5,658,893 A | 8/1997 | Anderson et al. |
| 6,391,452 B1 | 5/2002 | Antonsen et al. |
| 6,623,727 B2 | 9/2003 | Birkel et al. |
| 2003/0181416 A1 | 9/2003 | Comper |
| 2005/0261240 A1 | 11/2005 | Maguire et al. |
| 2006/0078504 A1* | 4/2006 | Yamamoto et al. ............ 424/45 |
| 2008/0184618 A1* | 8/2008 | Darlington ............. A01N 59/00 44/443 |
| 2008/0241271 A1* | 10/2008 | Roman et al. ................ 424/641 |

FOREIGN PATENT DOCUMENTS

| EP | 0 293 826 A2 | 12/1988 |
| EP | 1 108 422 A2 | 6/2001 |
| JP | A 11-080003 | 3/1999 |
| JP | A 2001-181188 | 7/2001 |
| JP | A 2003-081841 | 3/2003 |
| WO | WO/1998/006396 | 9/1988 |
| WO | WO 94/15624 | 7/1994 |
| WO | WO 01/80807 A2 | 11/2001 |
| WO | WO 02/02189 A2 | 1/2002 |
| WO | WO 2005/004882 AI | 1/2005 |
| WO | WO 2006/003521 A1 | 1/2006 |

OTHER PUBLICATIONS

Centers for Disease Control and Prevention, "Vaccine Effectiveness—How Well Does the Flu Vaccine Work?", two pages; page last updated Oct. 13, 2011; can be accessed at http://www.cdc.gov/flu/about/qa/vaccineeffect.htm.*
Centers for Disease Control and Prevention: "Adenovirus-Symptoms"; page last updated Dec. 27, 2011.*
Turner, Ronald, Merck Manual Professionals, "Respiratory Viruses: Common Cold", two total pages; last review/revision Oct. 2009; also can be accessed at http://www.merckmanuals.com/professional/print/infectious_diseases/respiratory_viruses/common_cold.html.*
Turner, Ronald, Merck Manual Professionals, "Respiratory Viruses: Adenovirus Infection", total two pages; last reviewed/revised Oct. 2009; also can be accessed at http://www.merckmanuals.com/professional/print/infectious_diseases/respiratory_viruses/adenovirus_infection.html.*
WordNet Search 3.0, "prevent", also can be accessed at http://wordnetweb.princeton.edu.*
Heikkinen, Terho et al., The Lancet, "The common cold", 2003, vol. 361,,p. 51-59.*
Makela, Mika J. et al., Journal of Clinical Microbiology, "Viruses and Bacteria in the Etiology of the Common Cold", 1998, vol. 36, No. 2, pp. 539-542.*
Kanemitsu, A. et al., English machine translation of JP 11-080003, published Mar. 1999, total 5 pages.*
Malhotra et al., "Isolation and characterization of potential respiratory syncytial virus receptor(s) on epithelial cells," Microbes and Infection, vol. 5, 2003, pp. 123-133.
Gonzalez et al., "Polysaccharides as Antiviral Agents: Antiviral Activity of Carrageenan," Antimicrobial Agents and Chemotherapy, vol. 31, No. 9, Sep. 1987, pp. 1388-1393.
Girond et al., "Antiviral activity of carrageenan on hepatitis A virus replication in cell culture," Res. Virol., vol. 142, 1991, pp. 261-270.
Baba et al., "Sulfated Polysaccharides Arc Potent and Selective Inhibitors of Various Enveloped Viruses, Including Herpes Simplex Virus, Cytomegalovirus, Vesicular Stomatitis Virus, and Human Immunodeficiency Virus," Antimicrobial Agents and Chemotherapy, vol. 32, No. 11, Nov. 1988, pp. 1742-1745.

(Continued)

*Primary Examiner* — Shaojia A Jiang
*Assistant Examiner* — Bahar Craigo
(74) *Attorney, Agent, or Firm* — Oliff PLC

(57) ABSTRACT

The present invention provides for the use of iota- and/or kappa-carrageenan for the manufacture of an antiviral pharmaceutical composition for the prophylaxis or treatment of a pathological condition or disease caused by or associated with an infection by a respiratory virus selected from the group consisting of orthomyxovirus, paramyxovirus, adenovirus and coronavirus. The present invention further provides for the use of fucoidan, in particular of high molecular weight fucoidan, for the manufacture of an antiviral pharmaceutical composition for the prophylaxis or treatment of a pathological condition or disease caused by or associated with an infection by a respiratory virus selected from the group consisting of orthomyxovirus and paramyxovirus.

26 Claims, 10 Drawing Sheets

(56) References Cited

OTHER PUBLICATIONS

Damonte et al., "Sulfated Seaweed Polysaccharides as Antiviral Agents," Current Medical Chemistry. 2004, vol. 11, pp. 2399-2419.
Turner et al., "Interferon Induction by the Immunomodulating Polyanion Lambda Carrageenan," Infection and Immunity, vol. 25, No. 1, Jul. 1979, pp. 467-469.
Fujisawa et al., "Protective Mechanisms against Pulmonary Infection with Influenza Virus. I. Relative Contribution of Polymorphonuclear Leukocytes and of Aleveolar Macrophages to Protection during Early Phase of Intranasal Infection," J. gen. Virol., vol. 68, 1987, pp. 425-432.
International Search Report issued in corresponding International Application No. PCT/EP2008/006910, dated Jan. 20, 2009.
Written Opinion of the International Searching Authority issued in corresponding International Application No. PCT/EP2008/006910, dated Jan. 20, 2009.
International Preliminary Report on Patentability issued in corresponding International Application No. PCT/EP2008/006910, completed Nov. 30, 2009.
Centers for Disease Control and Prevention, "Vaccine Effectiveness—How Well Does the Flu Vaccine Work?", 2 pages, page last updated Oct. 13, 2011; can be accessed at http://www.cdc.gov/flu/about/qa/vaccineeffect.htm.
Food and Drug Administration, U.S. Department of Health and Human Services, "Guidance for Industry: Container Closure Systems for Packaging Human Drug and Biologics", May 1999, total 56 pages.
Tsintsadze, Ted, Annals of Biomedical Research and Education, "Application of Antiviral Preparation "Super Lysine Plus" in a Complex of Treatment of Chronic Recurrent Herpetic Stomatitis", Apr./Jun. 2004, vol. 4, issue 2, pp. 92-93.
Turner, Ronald, Merck Manual Professionals, "Respiratory Viruses: Common Cold", 2 total pages; last review/revision Oct. 2009; also can be accessed at htpp://www.merckmanuals.com/professional/print/infectious_diseases/respiratory_viruses/common_cold.html.
Turner, Ronald, Merck Manual Professionals, "Respiratory Viruses: Adenovirus Infection", 2 total pages; last review/revision Oct. 2009; also can be accessed at htpp://www.merckmanuals.com/professional/print/infectious_diseases/respiratory_viruses/adenovirus_infection.html.
WordNet Search 3.0, "prevent", also can be accessed at http://wordnetweb.princeton.edu/perl/webwn?s=prevent&o2=$o0=1&o8=1&o1=1&o7=&o5=&o9=&o6=&o3=&o4=&h=; last viewed Mar. 10, 2012.

* cited by examiner

ANTIVIRAL COMPOSITION COMPRISING A SULFATED POLYSACCHARIDE

This is a Continuation of application Ser. No. 12/673,145 filed Feb. 24, 2010, which in turn is a Continuation of Application No. PCT/EP2008/006910 filed Aug. 22, 2008, which claims the benefit of U.S. Provisional Application No. 60/935,668 filed Aug. 24, 2007. The disclosures of the prior applications are hereby incorporated by reference herein in their entirety.

TECHNICAL FIELD

The present invention relates to sulfated polysaccharides selected from the group of carrageenans and fucoidans and pharmaceutical compositions made thereof, wherein said sulfated polysaccharides are present as antiviral active ingredients, for medical or veterinary use in the prevention or treatment of diseases caused by or associated with a virus entering an individual's body via the respiratory tract, the virus being selected from the group of orthomyxoviridae, paramyxoviridae, adenoviridae and coronaviridae.

BACKGROUND OF THE INVENTION

Orthomyxoviridae are RNA viruses, the most prominent members being influenza virus species. Influenza A and B virus are the two types of influenza viruses that cause epidemic human disease. They are typically spread from person to person, primarily through respiratory droplet transmission.

The paramyxoviridae family includes respiratory syncytial virus (RSV), parainfluenza virus and metapneumavirus. RSV and parainfluenza virus infections may cause serious respiratory infections in infants and young children but may also cause severe disease in elderly persons and adults having an impaired immune system.

Among the human parainfluenza virus species four members are known to cause serious respiratory diseases in children for which presently no effective prevention or therapy is available, the four members being parainfluenza virus types 1 through 4. Parainfluenza virus and RSV outbreaks are believed to contribute substantially to increased hospitalization and mortality rates. Patients with impaired immune, cardiac, or pulmonary systems are at increased risk of running into serious complications following a paramyxovirus infection and will therefore particularly benefit from an antiviral therapy.

Respiratory syncytial virus (RSV), which is the most wide-spread respiratory pathogen typically afflicting individuals during infancy and early childhood worldwide, causes yearly outbreaks of pneumonia and bronchiolitis during winter time and early in spring. RSV bronchiolitis and pneumonia require hospitalization of hundreds of thousands of infants every year. Passive protection against RSV is available at least in part at a reported 55% success rate upon monthly intramuscular injection of the humanized monoclonal anti-RSV antibody palivizumab (Synagis®).

The coronaviridae family includes coronavirus and torovirus. Coronaviruses are known to infect the upper respiratory tract and the gastrointestinal tract in mammals and birds. It is believed that coronaviruses cause a high percentage of all common colds in human adults.

Adenoviridae are DNA viruses which typically infect the upper respiratory tract. At present, more than 50 different serotypes of human adenovirus are known, grouped in six subtypes A to F, which are responsible for 5-10% of upper respiratory infection in children.

In view of the aforementioned it is believed that there exists a strong need for a potent antiviral pharmaceutical composition that is easily applicable and effective in the prevention or treatment of respiratory viral infections caused by members of the paramyxoviridae, orthomyxoviridae, coronaviridae and/or adenoviridae families.

Sulphated polysaccharides including carrageenans and fucoidan have been known for their antiviral efficacy for decades. Accordingly, the prior art is replete with scientific articles on the antiviral effects of carrageenans. In a most interesting review, Gonzalez M. E. et al. (1987, Antimicrob. Agents Chemother. 31, 1388-1393) report an antiviral efficacy of different sulphated polysaccharides including iota-carrageenan against several animal viruses. Iota-carrageenan showed antiviral activity against the enveloped viruses HSV-1, HSV-2, Semliki Forest virus (SFV), vaccinia virus and African swine fever virus (ASF) and against the naked encephalomyocarditis (EMC) virus. Iota-carrageenan had no effect on the enveloped viruses vesicular stomatitis virus (VSV) and measles virus and on the naked viruses polio virus type 1 and adenovirus type 5.

U.S. Pat. No. 4,783,446 discloses an antiviral activity of iota-, kappa- and lambda-carrageenan against retroviral infection, in particular against human T-cell leukemia virus (HTLV) III infection.

WO 88/06396 discloses a method for the treatment of retroviral infections, including infection with HIV, by administering a carrageenan or a mixture of carrageenans.

Girond et al. (1991, Research Virol. 142, 261-270) disclose that sulphated polysaccharides like iota-, kappa-, and lambda-carrageenan have an effective inhibitory activity against the replication of hepatitis A virus (HAV).

Baba M. et al. (1988, Antimicrob. Agents Chemother. 32, 1742-1745) disclose several sulphated polysaccharides including dextran sulphate, pentosan polysulphate, fucoidan and carrageenan as being potent inhibitors of HSV-1, HSV-2, human cytomegalovirus (CMV), vesicular stomatitis virus (VSV), Sindbis virus and HIV-1. On the other hand, these sulphated polysaccharides were tested to be inactive against coxsackievirus, poliovirus and parainfluenza virus.

EP 0293826 discloses the therapeutic and prophylactic application of sulfated polysaccharides such as fucoidan and carrageenans to inhibit HIV-1 in vitro.

U.S. Pat. No. 5,658,893 discloses a method for inhibiting rotavirus infection of human cells by contacting the rotavirus with lambda-carrageenan. It is further disclosed that iota- and kappa-carrageenan did not exhibit anti-rotaviral activity.

US 2003/181415 A discloses that sulphated polysaccharides, including cellulose sulphate, are known to be effective against various enveloped viruses and in particular against herpes simplex virus (HSV), Papilloma viruses and HIV.

Fucoidan is a sulphated polysaccharide mainly extracted from various species of brown seaweed. There are two types of pharmacological grade fucoidans available on the market, a high molecular weight fucoidan (HMWF) fraction having an average molecular weight ranging from about 1,000,000 to 2,000,000 Da (e.g. Kraeber, Germany) and a low molecular weight fucoidan (LMWF) fraction having an average molecular weight of 8,200 Da.

F-fucoidan is mainly composed of sulphated esters of fucose, while U-fucoidan is comprised of about 20% of glucuronic acid.

Carrageenan is a generic term for linear sulphated galactose-based polysaccharides extracted from seaweed (rhodophyceae). It is mainly used as a thickener, gelling agent, stabilizer or emulsifier in pharmaceutical and food products. There exist more than 10 structurally different carrageenans, their nature depending on the seaweed genus from which they are extracted. The three main types are iota-, kappa- and lambda-carrageenan, which differ slightly in their structure and degree of sulphatation. Iota-carrageenan is a soft-gel forming sulphated galactan predominantly extracted from red seaweed *Gigartina stellata* and *Chondrus crispus*. Kappa-carrageenan yields strong, rigid gels and is predominantly produced from *Kappaphycus cottonii*. Lambda-carrageenan, which is the most common form, is frequently used to thicken dairy products.

Despite the long known antiviral activity of carrageenans against viruses such as, e.g. HIV, HSV, HAV, HTLV, or HPV, the mechanism of how carrageenans exhibit antiviral activity still needs further clarification.

For example, Baba M. et al. (1988, Antimicrob. Agents Chemother. 32, 1742-1745) speculate that sulphated polysaccharides including kappa- and lambda-carrageenan inhibit or at least contribute to the inhibition of virus adsorption of several enveloped viruses to the host cell surface. Similarly, US 2005/0261240 assumes that carrageenan may non-specifically bind to a virus thereby blocking virus receptor sites. Damonte E. B. et al. (2004, Curr. Med. Chem. 11, 2399-2419) disclose that sulphated polysaccharides may mimic cellular heparin sulphate and therefore block viral receptor sites responsible for the initial interaction between virus and host cell, whereas Gonzalez M. E. et al. (1987, Antimicrob. Agents Chemother. 31, 1388-1393) found, using labeled virion particles, that HSV-1 virions are internalized even in the presence of high concentrations of iota-carrageenan. They suggest that at least for HSV-1 carrageenan inhibits a step in virus replication subsequent to virus attachment and entry into the cell but still prior to the synthesis of late viral proteins.

Turner E. V. and Sonnenfeld G. (1979, Infection and Immunity 25, 467-469) disclose an antiviral activity of lambda- but not kappa-carrageenan against bovine vesicular stomatitis virus which antiviral activity is due to immunomodulation, i.e. to the induction of interferon.

In conclusion, it can be summarized taking the words of U.S. Pat. No. 5,658,893, that "in view of the different responses by different viruses to sulphated polysaccharides, it is clear that the response of a particular virus to carrageenan cannot be predicted with certainty without experimentation. The mechanism by which sulphated polysaccharides, particularly the carrageenans, inhibit viral replication and infectivity may not be uniform as different investigators reported contradictory findings when working with different viruses and cell types. It would not be obvious to one skilled in the art that a substance such as a sulphated polysaccharide that is an effective inhibitor of one virus would demonstrate similar efficacy against another virus."

In the light of the above, the present invention now provides for a carrageenan- and/or fucoidan-based antiviral composition suitable in the prophylactic or therapeutic treatment of respiratory viral infections caused by members of the paramyxoviridae, orthomyxoviridae, adenoviridae and/or coronaviridae families. Contrary to the disclosure of Fujisawa H. et al. (1987, J. gen. Virol. 68, 425-423), who report that intranasal administration of carrageenan did not reduce the influenza A virus titer in mice but on the contrary even enhanced the animals' susceptibility to the virus depending on the amount of virus used for infection, it was now surprisingly found that carrageenan, in particular iota- and kappa-carrageenan, has indeed antiviral efficacy against various members of the orthomyxoviridae, paramyxoviridae, adenoviridae and coronaviridae.

Additionally, it was surprisingly found that fucoidan, particularly the high molecular weight fucoidan (HWMF) fraction, has antiviral efficacy against various members of the orthomyxoviridae and paramyxoviridae.

Accordingly, the present invention aims at providing an antiviral pharmaceutical composition suitable for the prevention or treatment of respiratory tract infections caused by a virus selected from the group consisting of orthomyxovirus, paramyxovirus, adenovirus and coronavirus, as well as for diseases or pathological conditions associated with such primary viral infections, such diseases or conditions comprising secondary viral or bacterial infections as well as bodily symptoms typically associated with any such primary or secondary infection including symptoms such as fever, pain, dizziness, shivering, sweating, and/or dehydration.

DESCRIPTION OF THE INVENTION

In a first embodiment the present invention relates to the use of carrageenan as an antiviral active ingredient in the manufacture of a pharmaceutical composition for the prophylaxis or treatment of a pathological condition or disease caused by or associated with an infection by a respiratory virus, wherein said respiratory virus comprises at least one protein attached to or integrated in its viral membrane, the protein capable of binding to a host cell via a receptor having at least one sugar moiety, the respiratory virus being selected from the group consisting of orthomyxovirus and paramyxovirus and the carrageenan being selected from the group consisting of iota- and kappa-carrageenan.

A "host cell" referred to herein is any eukaryotic cell that is naturally, i.e. under natural or natural-like conditions, targeted and penetrated by any of the viruses referred to hereinafter. For experimental and laboratory purposes it is state of the art to use host cell lines that are typically recognized as suitable in vitro models for testing the efficacy of physiologically active agents and which allow for at least some predictability of the results with regard to comparable human applications.

The present invention further relates to a pharmaceutical composition comprising iota- and/or kappa-carrageenan as an antiviral active ingredient and to applications thereof in the prevention or treatment of diseases caused by or associated with a virus entering an individual's body via the respiratory tract, wherein said virus comprises at least one protein attached to or integrated in its viral membrane, the protein capable of binding to a host cell via a receptor having at least one sugar moiety, and the virus being selected from the group consisting of orthomyxovirus and paramyxovirus.

The term "antiviral active ingredient" as used herein refers to a compound that is directly or indirectly effective in specifically interfering with at least one viral action selected from the group consisting of virus penetration of eukaryotic cells, virus replication in eukaryotic cells, virus assembly, virus release from infected eukaryotic cells, or that is effective in unspecifically inhibiting a virus titer increase or in unspecifically reducing a virus titer level in a eukaryotic or mammalian host system. It also refers to a compound that prevents from or reduces the likelihood of getting a viral infection.

The present pharmaceutical composition may be administered, as the case may be, before or after the onset of a viral infection, i.e. for prophylactic or therapeutic treatment purposes, or for both prophylactic and therapeutic administration.

The term "prophylaxis" or "prophylactic treatment" as used herein relates to the administration of the present pharmaceutical composition to a healthy individual in order to reduce said individual's susceptibility for a viral infection.

The term "therapy" or "therapeutic treatment" as used herein relates to the administration of the present pharmaceutical composition in order to achieve a reduction in severity and/or frequency of symptoms, elimination of symptoms and/or underlying cause, prevention of the occurrence of symptoms and/or their underlying cause, and/or improvement or remediation of damage directly caused by or indirectly associated, e.g. through secondary infection, with the viral infection.

It is known that orthomyxo- and paramyxoviruses and several other viruses attach to the host cell via binding to receptors present on the host cell surface, the receptors typically being glycoproteins or glycolipids containing sugar residues including sialic acid (N-actyl neuramic acid) and heparan sulphate residues.

In the case of orthomyxoviruses, e.g. influenza viruses, the virions bind to sialic acid residues. Human influenza viruses preferably bind to sialic acid residues having an alpha 2-6 linkage, whereas avian influenza virus preferably bind to sialic acid residues having alpha 2-3 linkage.

The cellular uptake of a paramyxovirus involves at least two of its integral membrane glycoproteins. One of them, typically selected from the group of glycoproteins HN, H and G, is involved in cell attachment and the other glycoprotein, i.e. glycoprotein F, is involved in mediating pH-independent fusion of the viral envelope with the membrane of the host cell. For example, respiroviruses and rubulaviruses bind to sialic acid residues of glycoprotein or glycolipid host cell receptors.

The attachment of RSV is not fully understood but attachment to the host cell most likely involves interaction with heparan sulphate, a glucoseaminoglycan that is part of the extracellular matrix.

Along with revealing the present invention it was observed in vitro that exposing host cells to carrageenan, in particular iota- and/or kappa-carrageenan, may alter the structure of the cell surface of a said host cell, presumably by causing conformational changes in the three dimensional structure of certain cell surface receptors or by masking and/or modifying said receptors.

Surprisingly, this change on the host cell surface prevented orthomyxo- and paramyxoviruses from attachment to the host cells even after removal of the carrageenan from the host cells, i.e. in the absence of carrageenan at the time of artificially triggering an infection by inoculation in vitro.

This particular antiviral effect of carrageenan was observed as long as the artificially triggered infection was initiated no later than about two hours after removal of the polymer from the host cells, indicating a relatively long lasting effect of the structural changes on the cell surface caused by interaction with carrageenan.

In contrast to paramyxo- and orthomyxoviruses, a protective effect in the absence of carrageenan at the time of triggering infection was not observed for other viruses including rhinovirus and coronavirus, while protection was only achieved in the presence of carrageenan.

Therefore and in view of the experimentally proven antiviral efficacy of carrageenan against rhinovirus infection, it is concluded that with rhinovirus and probably other viruses, too, the antiviral effect may be due to attachment of the carrageenan polymer to the virions rather than to chemical or physical interaction of the polymer with the host cell receptors.

As mentioned herein before the carrageenan compositions of the present invention may successfully be applied against orthomyxovirus infection, including infections caused by influenza A or B virus, and especially wherein said influenza A or B virus is a human virus that binds to a host cell via 2-6 sialic acid linkage. Human influenza virus infections are best treated using predominantly or solely iota-carrageenan or fucoidan as the antiviral active ingredients.

Carrageenan may, however, also be successfully applied against infections wherein said influenza A virus is an avian virus that binds to a host cell via 2-3 sialic acid linkage. In this latter case, kappa-carrageenan turned out to be the most efficacious carrageenan, the use of which is therefore preferred in connection with avian virus prophylaxis or therapeutic treatment. Whereas iota-carrageenan and fucoidan were found to be much less active or even inactive towards avian influenza A virus.

The paramyxovirus species found to be susceptible to carrageenan treatment are selected from the group consisting of human parainfluenza virus (HPV) type 1, HPV type 2, HPV type 3, HPV type 4 and RSV. Where the selected paramyxovirus is RSV it is preferred that iota-carrageenan or fucoidan be applied as a predominant or sole sulfated polysaccharide ingredient for prophylactic or therapeutic administration, because iota-carrageenan and fucoidan yielded the best results in the experimental set-ups.

The pathological conditions or diseases referred to herein in connection with prophylactic or therapeutic administration of carrageenan comprise acute bronchitis, chronic bronchitis, rhinitis, sinusitis, croup, acute bronchiolitis, pharyngitis, tonsillitis, laryngitis, tracheitis, asthma and pneumonia.

Carrageenan is especially suitable for topical application to treat skin or mucosal inflammation. Carrageenan useful for topical application to the skin or mucosa in accordance with the present invention has a molecular weight ranging from about 15,000 to 5,000,000 Da, fractions having average molecular weights of more than 50,000 Da, and especially fractions having average molecular weights in the range of from 50,000 to 3,000,000 Da being particularly preferred.

Systemic, e.g. parenteral or oral administration is possible, too, especially using lower molecular weight polymers having an average molecular weight in the 15,000 to 100,000 Da range.

The pharmaceutical composition according to the present invention adjusted for parenteral use may be provided as a preparation selected from the group of skin lotions, creams, ointments, gels, powders including powders for inhalation, sprays, foams, liquid drops or gargle solutions. The carrageenan preparations may, however also be adjusted for oral administration, e.g. as liquid solutions, or semi-solid or solid preparations such as dry powders, tablets, capsules, dragees or any other orally ingestible galenic form. Pharmaceutical compositions for mucosal application include nose sprays or drops and any other nasal drug delivery system known in the art such as disclosed, for example, in U.S. Pat. No. 6,391, 452.

Where the composition is for topical use and is liquid or semi-solid it typically comprises in its ready-for-use form carrageenan in an amount of between 0.01 and 10%, preferably between 0.01 and 5%, most preferably between 0.1 and 2% by weight, relative to the total volume of the composition. Where the composition is solid it typically comprises in its ready-for-use form carrageenan in an amount of between 0.01 and 10%, preferably between 0.01 and 5%, most preferably between 0.1 and 2% by weight relative to the total weight of the composition.

The carrageenans useful in the present invention are commercially available but may also be prepared by extraction from seaweed plants pursuant to extraction procedures known in the art.

If not indicated otherwise the term "carrageenan" as used herein refers to either iota-, or kappa-carrageenan or a mixture of both.

The carrageenan of the present invention can further be a homopolymer or a heteropolymer. A carrageenan homopolymer is built of subunits of only one kind of either iota-, or kappa-carrageenan, whereas a carrageenan heteropolymer comprises subunits of both said carrageenans.

A "mixture" of carrageenans may thus also refer to a composition of matter comprising a mixture of different carrageenan subunits as part of at least one heteropolymeric carrageenan present in said composition.

Typically, the antiviral pharmaceutical compositions according to the present invention are substantially free of carrageenans other than iota- and kappa-carrageenan, i.e. comprise either iota- or kappa-carrageenan, or a mixture of both, in an amount of 80% or more, preferably of 90% or more, and especially of up to 99% (w/w) or more, relative to the dry weight of all carrageenans present in the composition.

For some applications the composition is substantially comprised solely of iota-carrageen, while for other applications the composition may comprise more than 50%, preferably more than 70%, and especially up to more than 95% (w/w) by dry weight of iota-carrageenan, relative to the total dry weight of all carrageenans present in the composition.

For still other applications it may be useful that the composition comprises more than 50%, preferably more than 70%, and especially up to more than 95% (w/w) by dry weight of kappa-carrageenan, relative to the total dry weight of all carrageenans present in the composition.

Where the composition comprises at least one heteropolymeric carrageenan the numeric values given above relate to the percentages of the respective carrageenan subunits.

The antiviral carrageenan compositions in accordance with the present invention may further comprise at least one pharmaceutically acceptable carrier and/or additive suitable and permitted for medical application.

The carrier may be a diluent, e.g. water, saline, optionally phosphate buffered saline (PBS), an excipient, or another vehicle which facilitates the administration of the composition. Where the composition is solid, semi-solid or fluid the groups of carriers and additives, respectively, may comprise but are not limited to $SiO_2$, $TiO_2$, a binder such as microcrystalline cellulose, polyvinylpyrrolidone, gum tragacanth, gelatine, starch, lactose, lactose monohydrate, alginic acid or maize starch; a lubricant or surfactant like magnesium stearate or sodium lauryl sulphate; a glidant like e.g. colloidal silicon dioxide; a sweetening agent such as sucrose or saccharin.

Still further additives may be selected from the group consisting of physiologically acceptable preservatives, pharmaceutically acceptable alkali metal salts like sodium, potassium, lithium or ammonium chlorides, buffers or pH adjusting agents such as citric acid, acetic acid, fumaric acid, hydrochloric acid, malic acid, nitric acid, phosphoric acid, propionic acid, sulphuric acid and tartaric acid, and combinations of said acids.

For many applications it is useful that the composition comprises sodium chloride as an additive.

Typically, a pharmaceutically acceptable salt is present in the composition in an amount of not more than 1%, preferably not more than 0.6% (w/v).

In the compositions of the present invention the carrageenan itself may be present as a salt, too, preferably as a sodium salt.

It is preferred that the present compositions for prophylactic or therapeutic medical application be provided as sterile, germ-free, pathogen-free, pyrogen-free and/or allergen-free preparations.

Carrageenan was found to be non-toxic upon oral or dermal administration, or upon inhalation, even when applied at extremely high doses. It was therefore classified as "generally recognized as safe" (GRAS) by the Food and Drug Administration (FDA).

Carrageenan, especially iota-carrageenan, can also be used as an antiviral agent effective against orthomyxovirus and paramyxovirus infections in various medicinal products together with other physiologically active compounds or drugs as the main active ingredients, wherein the role of carrageenan includes its use as a carrier or as an additive such as an emulsifier or a viscosity modifying agent. It is compatible with most pharmaceutical preparations without causing undesired side-effects.

It is therefore within the scope of the present invention to provide pharmaceutical compositions comprising carrageenan as an additive, more specifically as an antiviral, particularly anti-paramyxoviral or anti-orthomyxoviral, adjuvant to medicaments that are typically applied in the prophylaxis or therapy of infectious and/or inflammatory diseases, allergies and/or conditions of an impaired or suppressed immune system. In particular, it is within the scope of the present invention to use carrageenan, preferably iota-carrageenan, as an anti-influenza virus effective adjuvant in combination with medicaments useful in the prophylaxis or therapy of infectious and/or inflammatory diseases, allergies and/or conditions of an impaired or suppressed immune system.

It was observed that carrageenan may also have immunomodulating activity, particularly immune system strengthening activity. It is not yet clear, however, whether this activity is directly associated with a physiological interference of the substance or indirectly through its antiviral efficacy.

The composition of the present invention will usually be formulated into preparations for topical or mucosal use, preferably selected from sprays, particularly nose sprays, powders, drops, gargle solutions, foams, gels, creams, ointments, lotions, lozenges, and the like. However, the pharmaceutical composition of the present invention may also be coated onto solid surfaces of hygiene or sanitary items such as, for example, facial hygiene or sanitation articles that are typically used in the oral and/or nasal areas including but not limited to nasal tissues or papers, and handkerchiefs.

More specifically, the pharmaceutical composition may be applied, e.g. sprayed—much like disinfectants—onto gloves, hygiene tissues or papers including nasal tissues or papers, in order to exert a virucide effect at least to some extent, thus contributing to reducing an individual's repeated self-infection by contaminated fingertips and also to reduce viral distribution among different individuals that are in close, e.g. hand-to-hand, contact with each other.

Further items coated, impregnated or soaked with a pharmaceutical composition on a carrageenan basis comprise cotton swabs, dust masks or sanitary or medical facial masks. Even lipsticks can be formulated to contain an antiviral effective amount of carrageenan. These hygiene or sanitation articles can be used prophylactically or for therapeutical treatment against a viral infection and may assist in the prevention or reduction of a risk of infection.

It is an objective of the present invention to provide for carrageenan-based antiviral compositions for the prophylaxis or therapeutic treatment of individuals especially susceptible to or at increased risk of orthomyxo- or paramyxovirus infection including high-risk patients selected from the group consisting of COPD-patients, asthma patients, individuals suffering from allergies, or from impaired immune, cardiac, or pulmonary systems, and transplantation patients.

In accordance with the present invention carrageenan may also be used as an antiviral active ingredient in the manufacture of a pharmaceutical composition for the prophylaxis or therapeutic treatment of a pathological condition or disease caused by or associated with an infection by a respiratory virus being selected from the group consisting of adenovirus and coronavirus, the adenovirus preferably being adenovirus type B (Ad50).

Adenovirus and coronavirus infections are best treated using compositions where iota-carrageenan is the sole or predominant active antiviral ingredient.

Experimental trials further confirmed that also fucoidan is usefully applied as an antiviral active ingredient in the manufacture of a pharmaceutical composition effective for the prophylaxis or treatment of pathological conditions or diseases caused by or associated with a respiratory virus infection, the respiratory virus selected from the group consisting of orthomyxo- and paramyxoviruses. In this context, the orthmyxovirus is typically influenza virus A or B, and the paramyxovirus is typically RSV.

A fucoidan-based composition in its ready-for-use form for topical or oral administration may comprise fucoidan in an amount of between 0.01 and 10%, preferably between 0.01 and 5%, most preferably between 0.1 and 2% weight per volume (w/v) or weight per weight (w/w) depending on whether the composition is liquid or semi-solid (w/v-percentages) or solid (w/w-percentages). It may further comprise at least one pharmaceutically acceptable carrier and/or additive, as well as other physiologically active substances or drugs. For example, sodium chloride is frequently used as an additive. In general, pharmaceutically acceptable salts may be present in the fucoidan compositions in an amount of not more than 1%, preferably not more than 0.6%.

Ordinate=percentage of plaque formation after infection of MDCK cells with influenza A/Chile/1/93 H1N1 virus suspension containing different concentrations of iota-carrageenan relative to the plaque formation of MDCK cells infected with influenza A/Chile/1/93 H1N1 virus suspension without iota-carrageenan (set as 100%); abscissa=different final concentrations of iota-carrageenan in the virus suspension in µg/ml.

Figure 2:
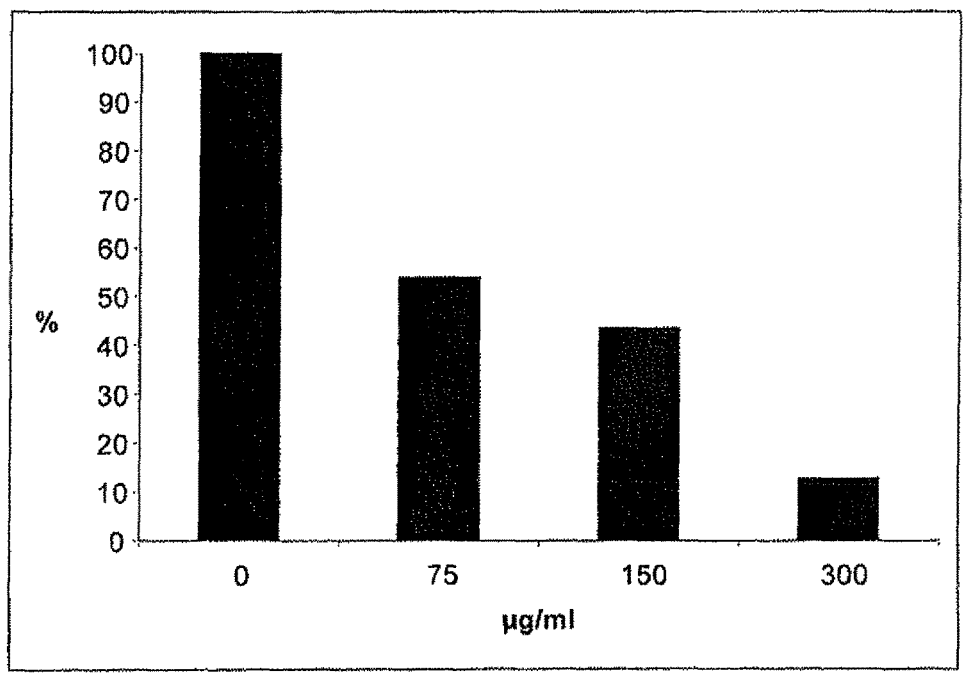

FIG. 2 shows the efficacy of iota-carrageenan in reducing plaque formation of influenza A/Aichi2/68 H3N2 virus in MDCK cells at different doses ranging from a final concentration of 75 to 300 µg/ml.

Ordinate=percentage of plaque formation after infection of MDCK cells with influenza A/Aichi2/68 H3N2 virus suspension containing different concentrations of iota-carrageenan relative to the plaque formation of MDCK cells infected with influenza A/Aichi2/68 H3N2 virus suspension without iota-carrageenan (set as 100%); abscissa=different final concentrations of iota-carrageenan in the virus suspension in µg/ml.

Figure 3:
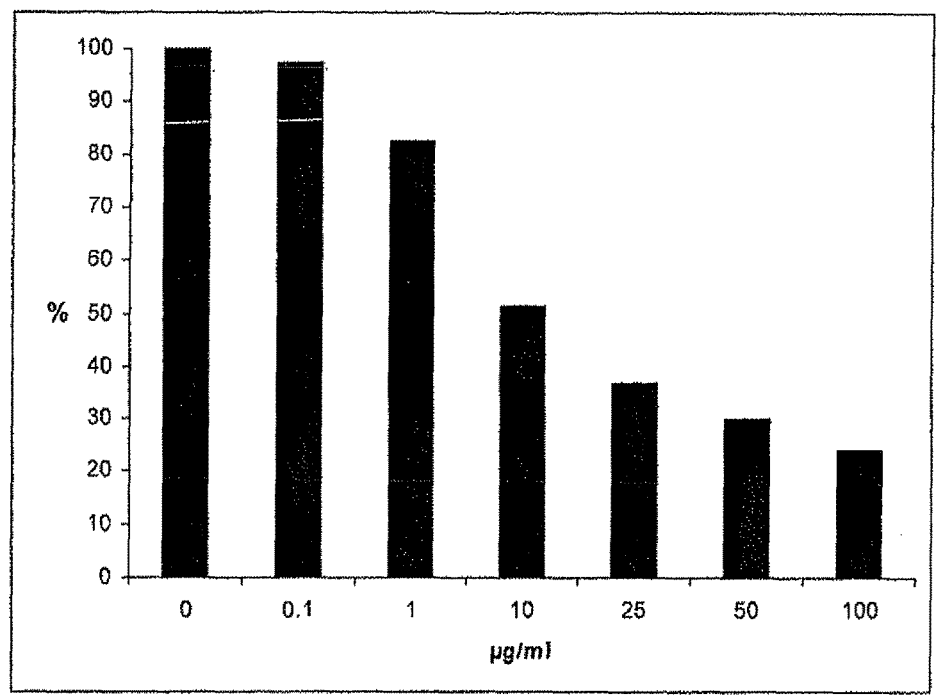

FIG. 3 shows the efficacy of iota-carrageenan in reducing plaque formation of parainfluenza virus 3 in Hep-2 cells at different doses ranging from a final concentration of 0.1 to 100 µg/ml.

Ordinate=percentage of plaque formation after infection of Hep-2 cells with parainfluenza virus 3 suspension containing different concentrations of iota-carrageenan relative to the plaque formation of Hep-2 cells infected with parainfluenza virus 3 suspension without iota-carrageenan (set as 100%); abscissa=different final concentrations of iota-carrageenan in the virus suspension in µg/ml.

Figure 4:
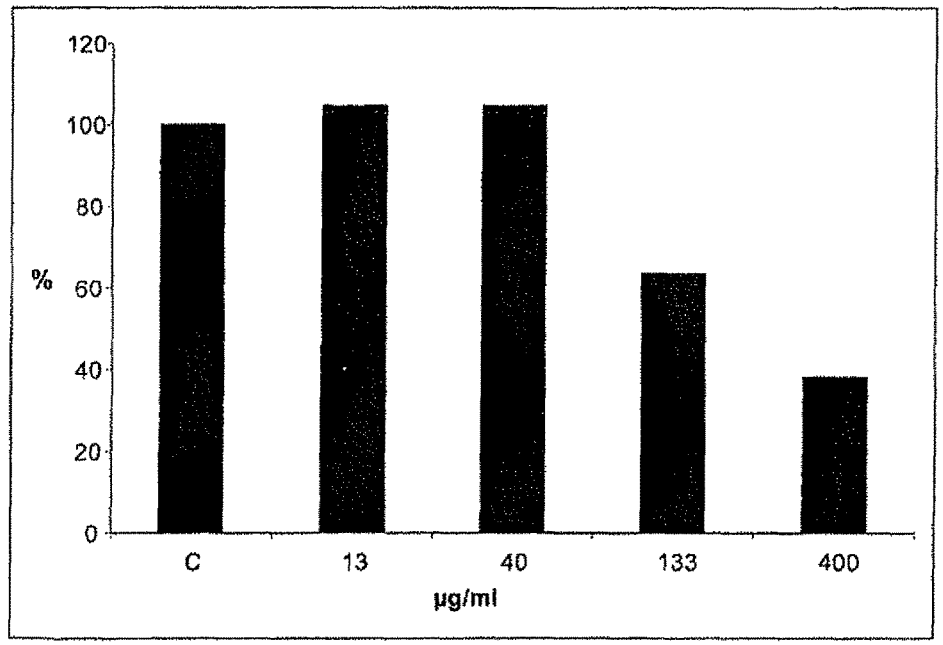

FIG. 4 shows the efficacy of iota-carrageenan pretreatment in reducing plaque formation of parainfluenza virus 3 in HeLa cells at different doses ranging from a final concentration of 13 to 400 µg/ml.

Ordinate=percentage of plaque formation after infection of pretreated HeLa cells (preincubation for 3 h with iota-carrageenan; subsequent removal of the polymer) with parainfluenza virus 3 suspension relative to the plaque formation of untreated HeLa cells (without iota-carrageenan preincubation) (set as 100%); abscissa=different final concentrations of iota-carrageenan in the preincubation medium in µg/ml. C=cells preincubated with polymer carboxymethylcellulose (negative control).

FIG. 5 shows the results of a coronavirus induced cell death inhibition experiment in cat kidney (CK) cells.

Figure 5A:
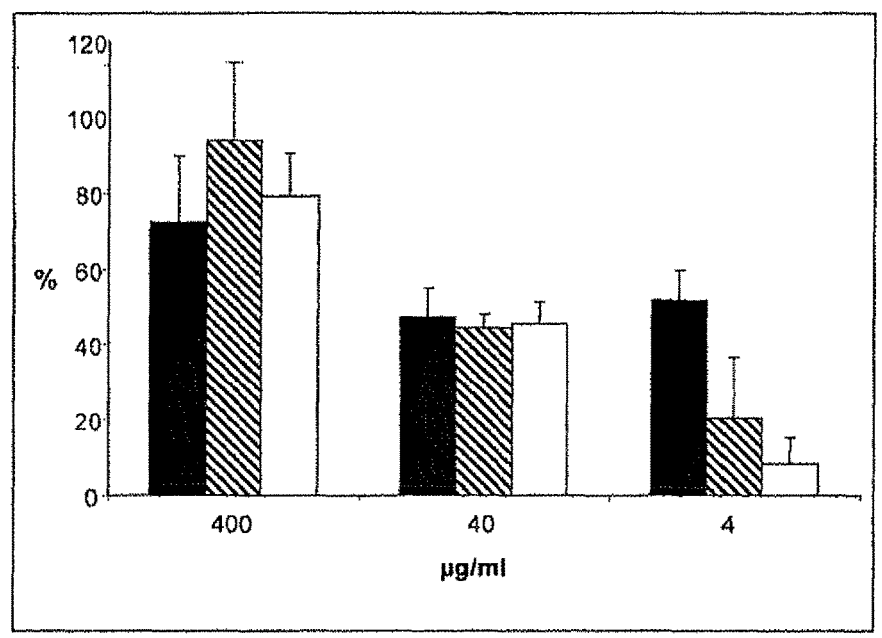
Figure 5B:
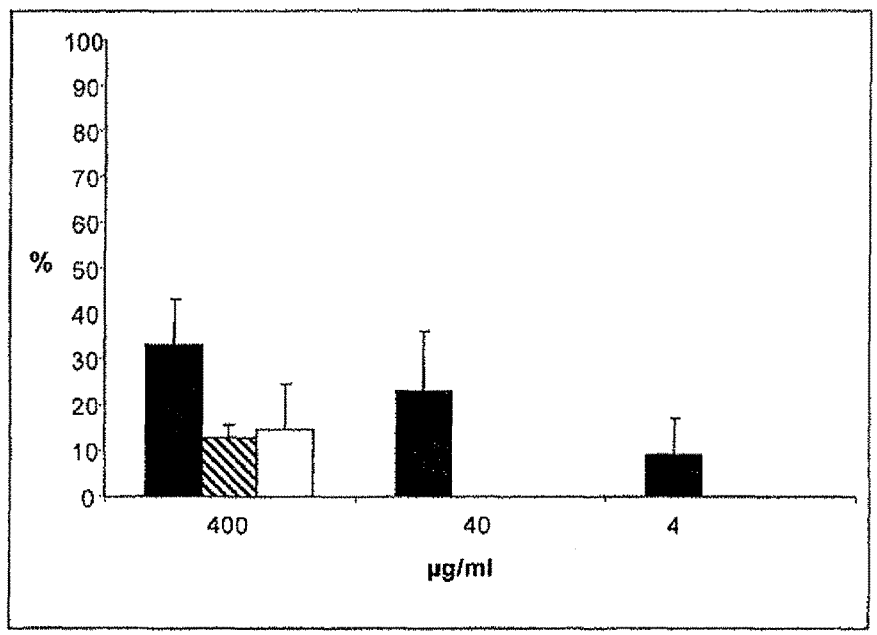

Ordinate=percentage of uninfected cells after infection relative to uninfected control cells; abscissa=different final concentrations of carrageenan in the virus suspension (FIG. 5A) or in the preincubation medium (FIG. 5B) in µg/ml; FIG. 5A=cells infected with feline coronavirus FIP in the presence of iota-, kappa- or lambda-carrageenan; FIG. 5B=cells preincubated for 3 h with iota-, kappa- or lambda-carrageenan, subsequently washed three times with PBS and infected with feline coroanvirus FIP in the absence of the polymer.

FIG. 6 shows the results of a HRV8 induced cell death inhibition experiment in HeLa cells.

Figure 6A:
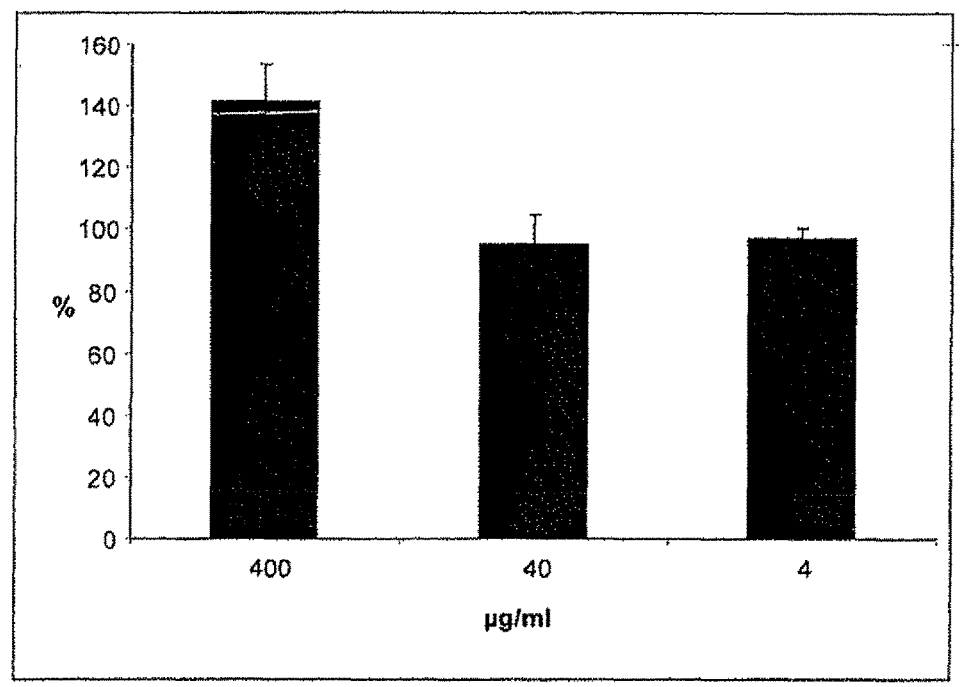
Figure 6B:
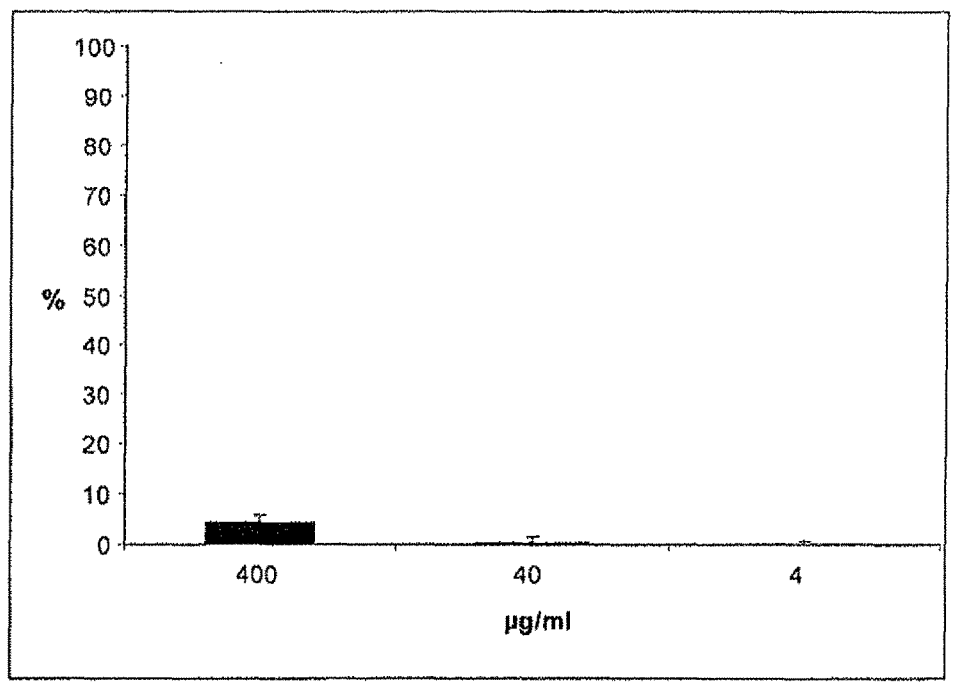

Ordinate=percentage of uninfected cells after infection relative to uninfected control cells; abscissa=different final concentrations of iota-carrageenan in the virus suspension (FIG. 6A) or in the preincubation medium (FIG. 6B) in µg/ml; FIG. 6A=cells infected with human rhinovirus type 8 (HRV8) in the presence of iota-carrageenan; FIG. 6B=cells preincubated for 3 h with iota-carrageenan, subsequently washed three times with PBS and infected with HRV8 in the absence of iota-carrageenan.

Figure 7:
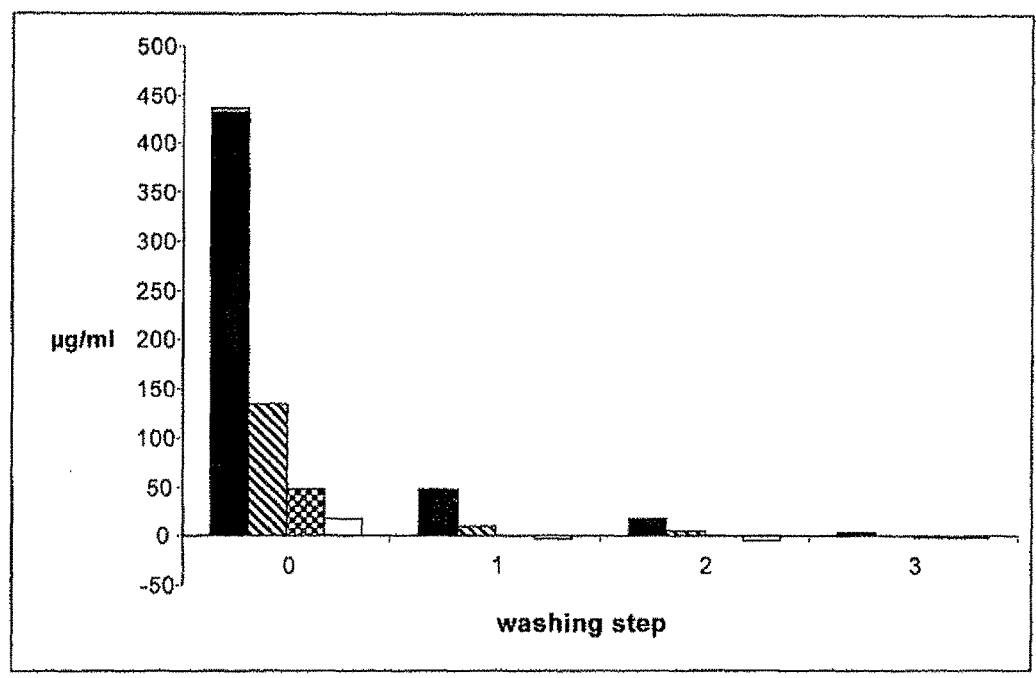

FIG. 7 shows the binding of FITC-labelled iota-carrageenan to HeLa cells after successive washing with PBS.

Ordinate=calculated iota-carrageenan (converted from fluorescent light units into µg/ml using a standard curve); abscissa=washing steps of the cells with PBS; 0=FITC-labelled iota-carrageenan containing supernatant was removed from the cells; 1=first washing step of the cells with PBS; 2=second washing step of the cells with PBS; 3=third washing step of the cells with PBS.

Figure 8:
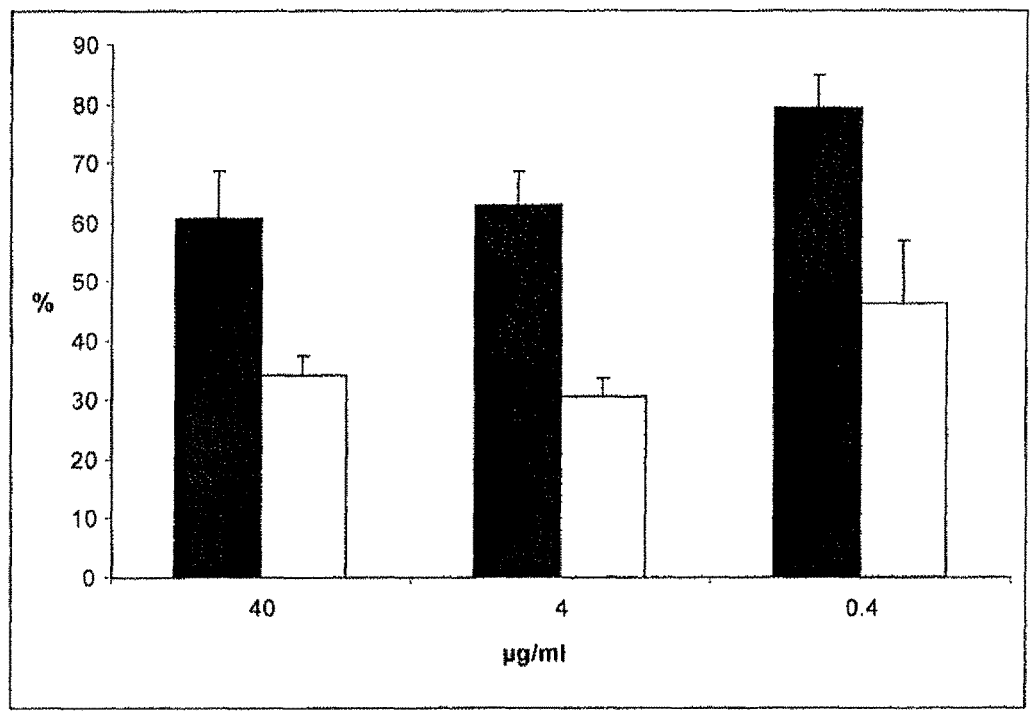

FIG. 8 shows the results of a RSV induced cell death inhibition experiment in Vero cells.

Ordinate=percentage of uninfected cells after infection relative to uninfected control cells; abscissa=different final concentrations of iota-carrageenan in the virus suspension (dark bars) or in the preincubation medium (light bars) in μg/ml; dark bars=cells infected with RSV in the presence of iota-carrageenan; light bars=cells preincubated for 3 h with iota-carrageenan, subsequently washed three times with PBS and infected with RSV in the absence of iota-carrageenan.

Figure 9:
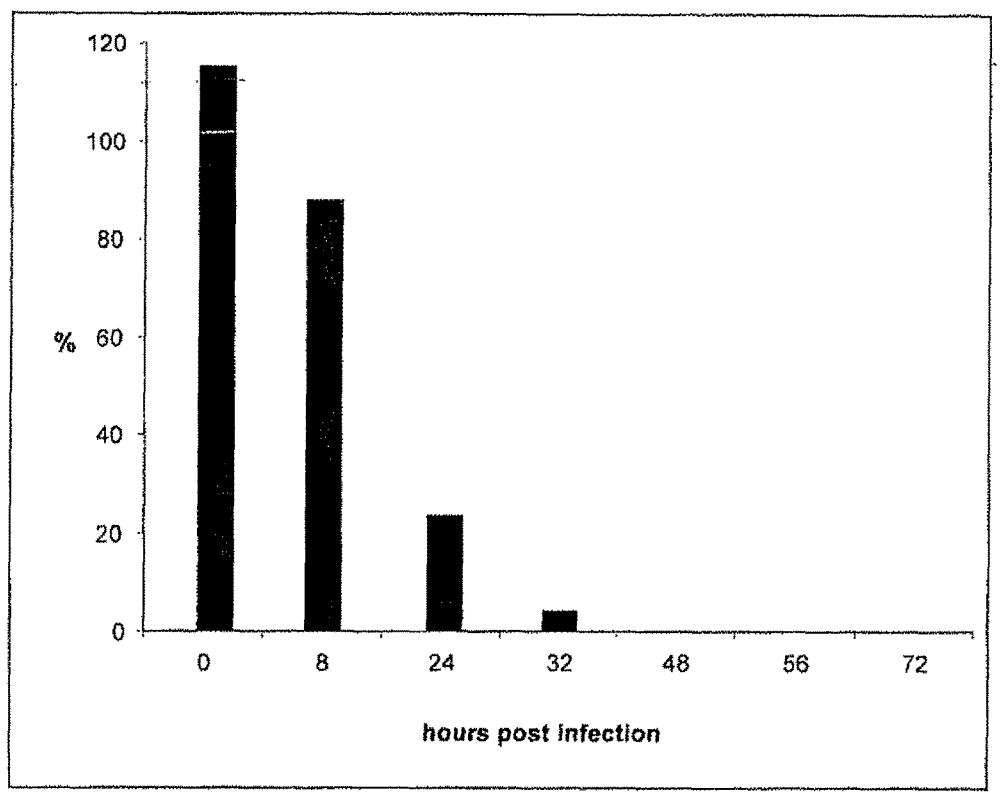

FIG. 9 shows the results of an RSV induced cell death inhibition experiment in HNep cells.

Ordinate=percentage of uninfected cells after infection and 5 days of incubation relative to uninfected control cells; abscissa=time points for addition of iota-carrageenan in a final concentration of 100 μg/ml to the incubation medium (hours post infection).

Figure 10:
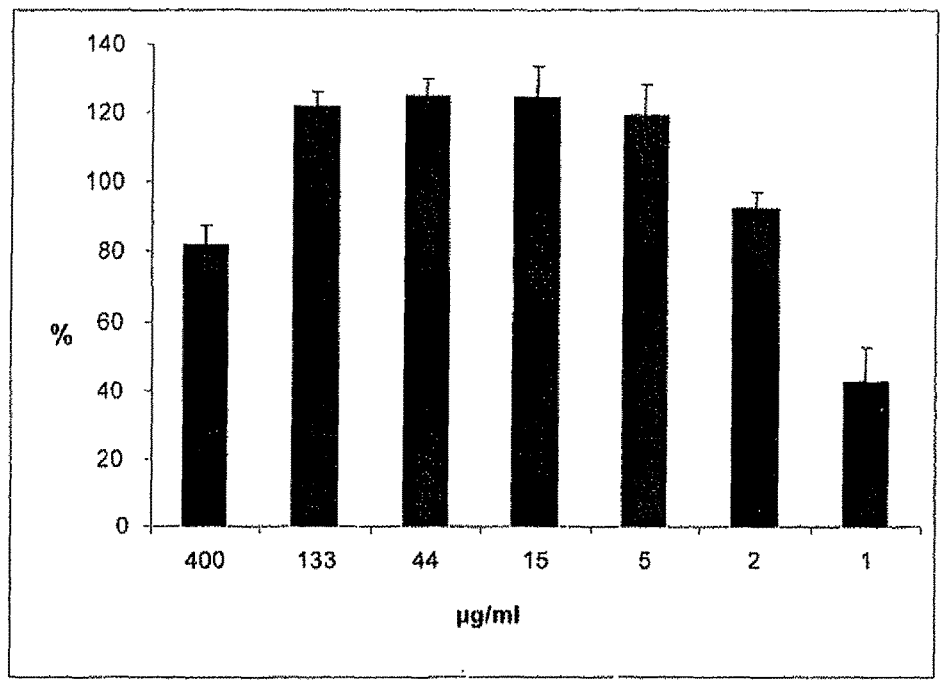

FIG. 10 shows the results of an RSV induced cell death inhibition experiment in HNep cells.

Ordinate=percentage of uninfected cells after infection and 5 days of incubation relative to uninfected control cells; abscissa=different final concentrations of iota-carrageenan in the virus suspension in μg/ml.

Figure 11:
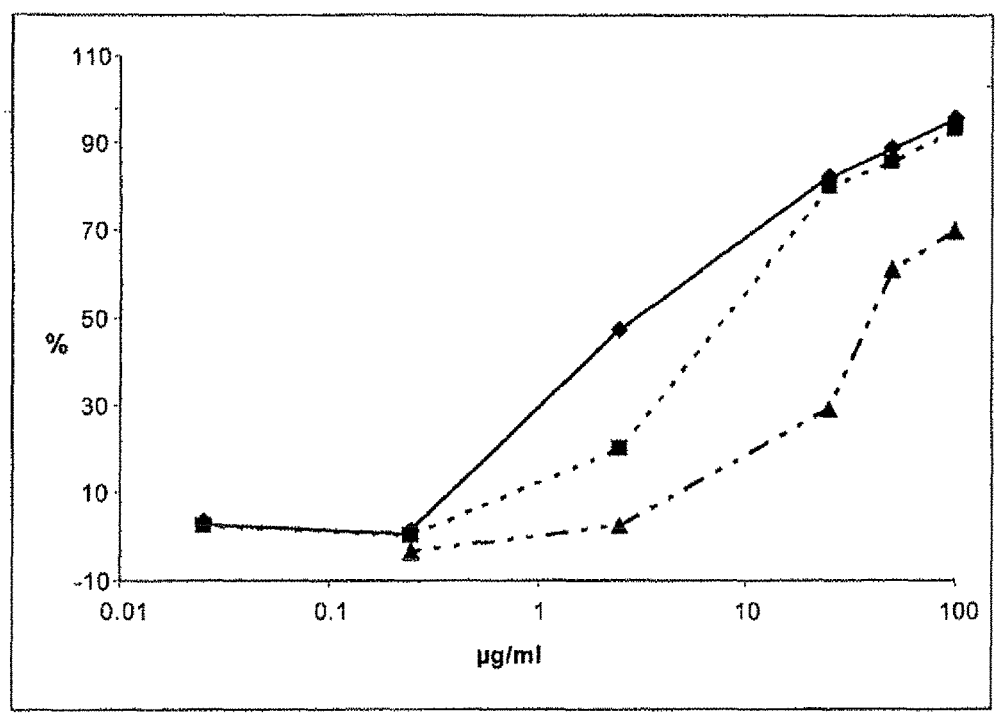

FIG. 11 shows the results of a RSV induced cell death inhibition experiment in HEp-2 cells.

Ordinate=percentage of uninfected cells after infection and 6 days of incubation at 37° C. relative to uninfected control cells; abscissa=different final concentrations of iota-, kappa- or lambda-carrageenan in the virus suspension in μg/ml.

Figure 12:
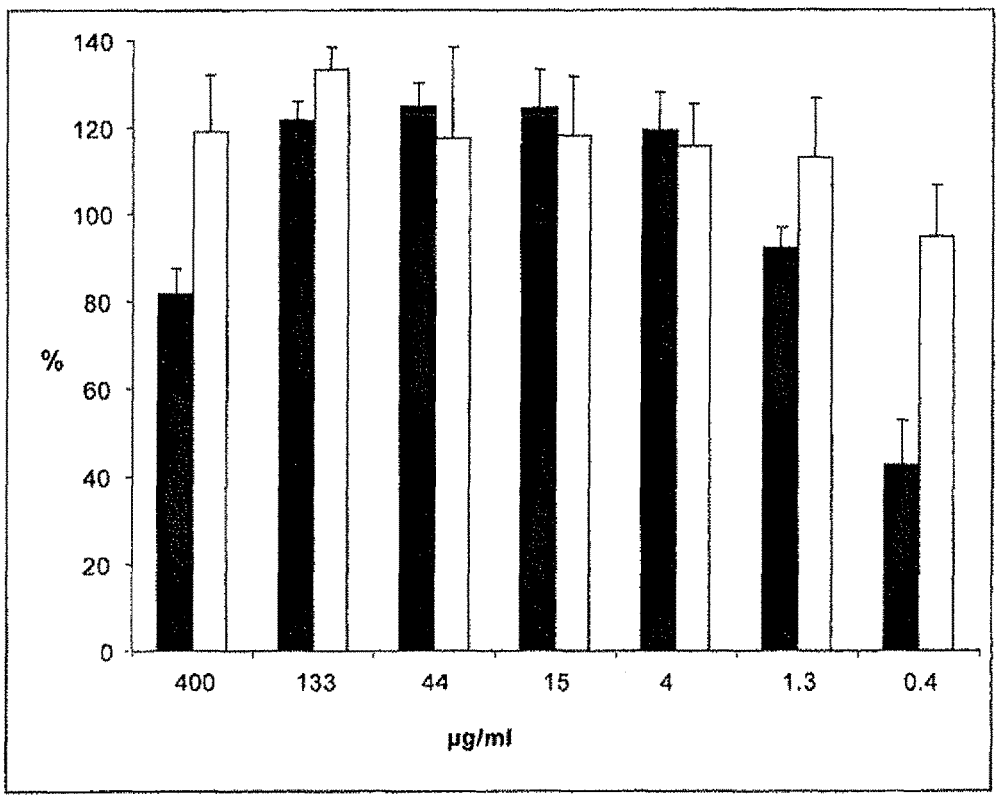

FIG. 12 shows the results of a RSV induced cell death inhibition experiment in HNep cells.

Ordinate=percentage of uninfected cells after infection relative to uninfected control cells; abscissa=different final concentrations of iota-carrageenan (dark bars) and fucoidan (light bars) in the virus suspension in μg/ml.

Figure 13:
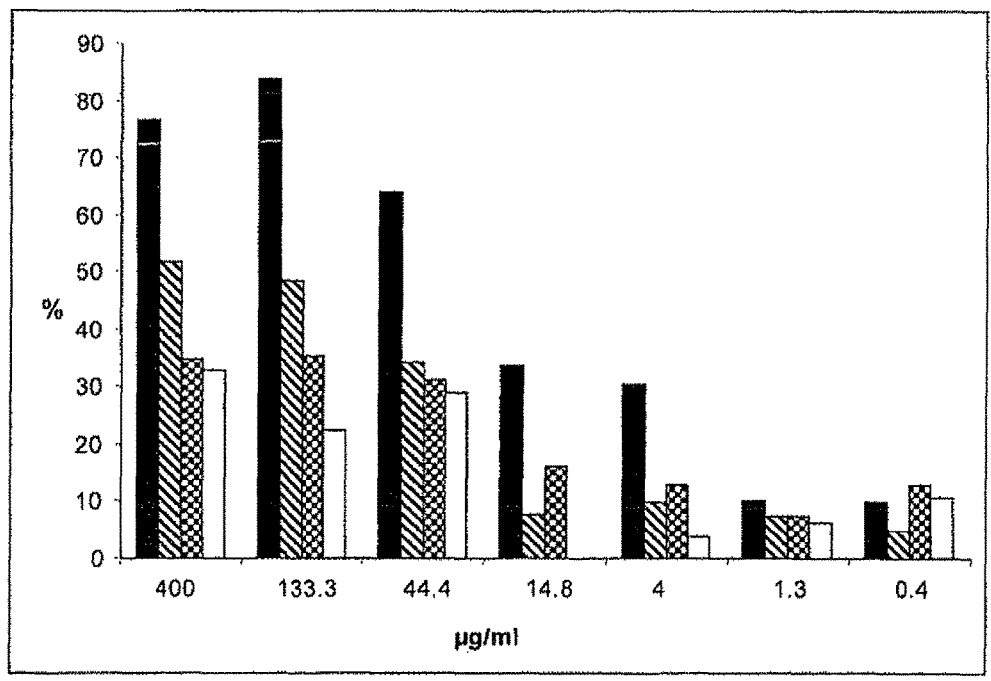

FIG. 13 shows the results of a parainfluenza virus 3 induced cell death inhibition experiment in HNep cells.

Ordinate=percentage of uninfected cells after infection relative to uninfected control cells; abscissa=different final concentrations of iota-, kappa- or lambda-carrageenan or fucoidan in the virus suspension in μg/ml.

Figure 14:
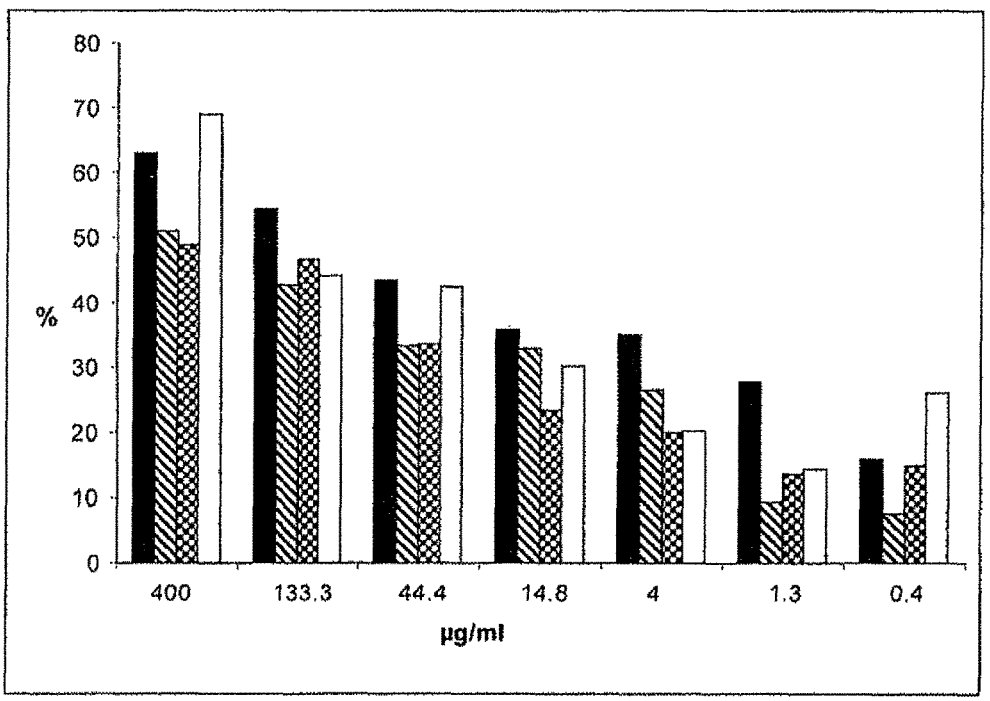

FIG. 14 shows the results of an influenza virus H3N2 (FLU) induced cell death inhibition experiment in HNep cells.

Ordinate-percentage of uninfected cells after infection relative to uninfected control cells; abscissa=different final concentrations of iota-, kappa- or lambda-carrageenan or fucoidan in the virus suspension in μg/ml.

Figure 15:
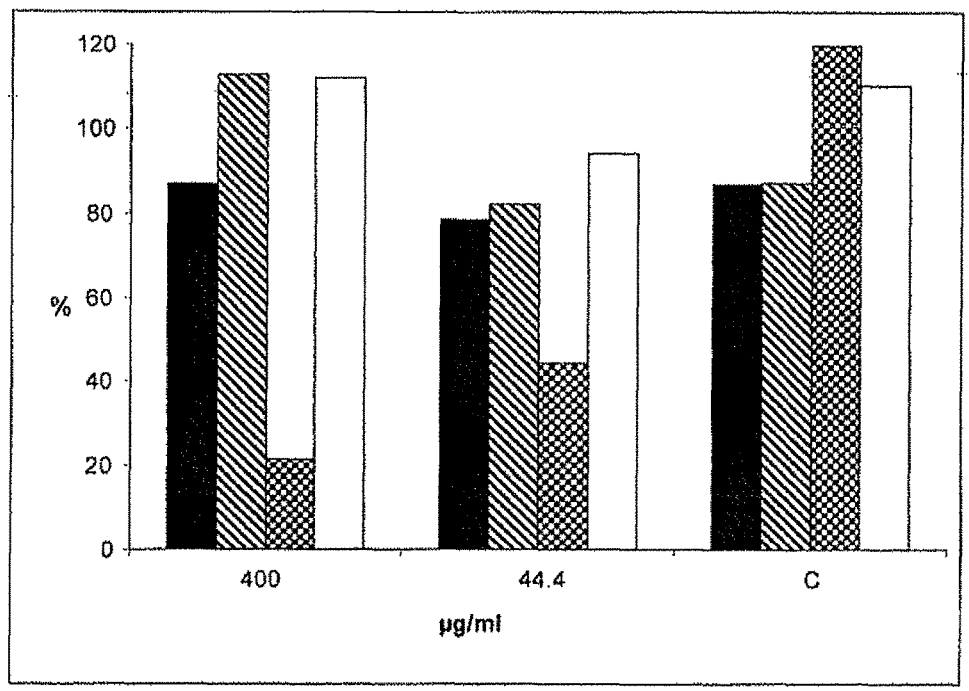

FIG. 15 shows the efficacy of iota-, kappa-, lambda-carrageenan and fucoidan in reducing plaque formation of influenza A H5N1 virus in MDCK cells at doses of 400 μg/ml and 44 μg/ml.

Ordinate=percentage of plaque formation after infection of MDCK cells with avian influenza H5N1 virus suspension containing different concentrations of iota-, kappa-, lambda-carrageenan or fucoidan relative to the plaque formation of MDCK cells infected with influenza H5N1 virus suspension without polymer (set as 100%); abscissa=different final concentrations of iota-, kappa-, lambda-carrageenan or fucoidan in the virus suspension in μg/ml.

Figure 16:
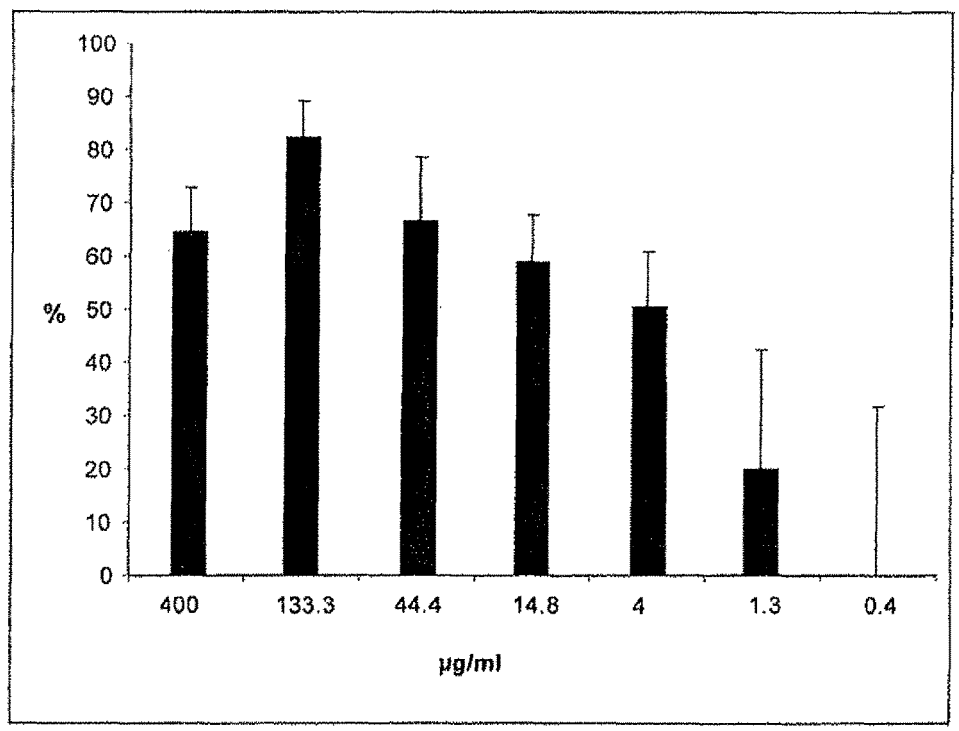

FIG. 16 shows the results of an adenovirus type 50 (Ad50) induced cell death inhibition experiment in HNep cells.

Ordinate=percentage of uninfected cells after infection relative to uninfected control cells; abscissa=different final concentrations of iota-carrageenan in the virus suspension in μg/ml.

Figure 17:
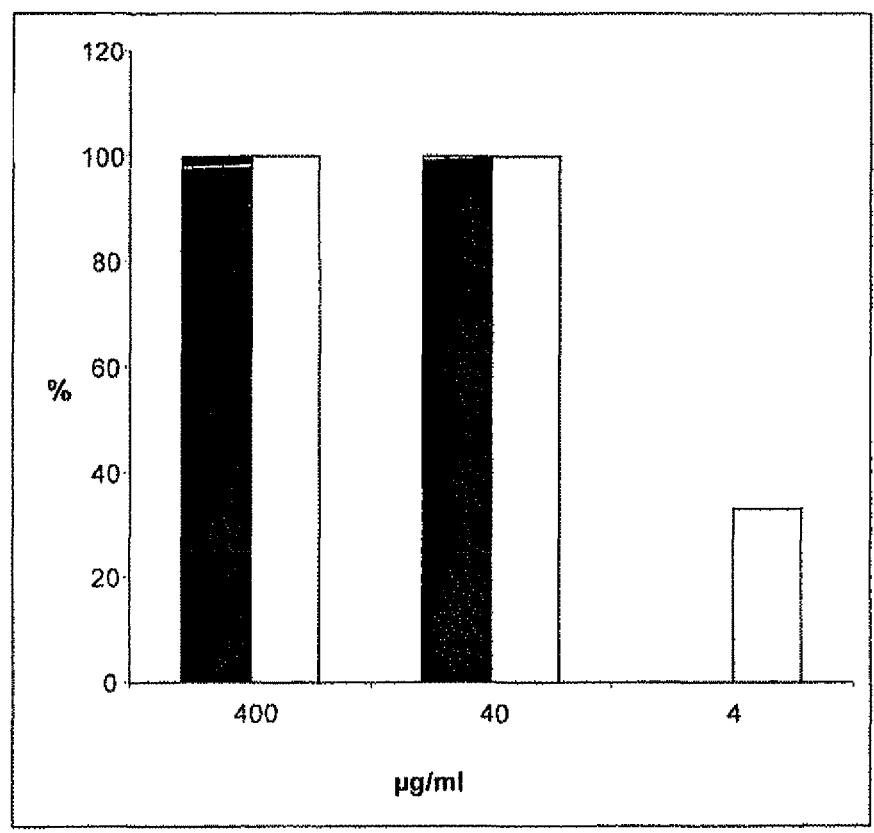

FIG. 17 shows the results of an Ad50 induced cell death inhibition experiment in HNep cells.

Ordinate-percentage of uninfected cells after infection relative to uninfected control cells; abscissa=different final concentrations of iota-carrageenan in the virus suspension (dark bars) or in the preincubation medium (light bars) in μg/ml; dark bars=cells infected with Ad50 in the presence of iota-carrageenan; light bars=cells preincubated for 3 h with iota-carrageenan, subsequently washed three times with PBS and infected with Ad50 in the absence of iota-carrageenan.

In order that the invention described herein may be more fully understood, the following examples are set forth. The examples are for illustrative purposes only and are not to be construed as limiting this invention in any respect. It is further understood that the present invention shall also comprise variations of the expressly disclosed embodiments to an extent as would be contemplated by a person of ordinary skill in the art.

EXAMPLES

Example 1: Effect of Different Concentrations of Iota-Carrageenan on Influenza A Virus Plaque Formation in MDCK Cells Virus suspensions containing 60-80 pfu of influenza virus A/Chile/1/93 H1N1 were mixed with a iota-carrageenan stock solution to final concentrations of 0.1, 1, 10, 25, 50 or 100 μg/ml. Confluent monolayers of the canine kidney cell line MDCK in six well plates were infected with the virus suspensions for 60 min at 34° C. The infection inoculum was removed and cells were washed with PBS and agarose overlay containing 0.6% agarose was added. Plates were incubated at 36° C. in a humidified atmosphere of 5% $CO_2$ in air. 48-60 h after infection the agarose overlay was removed, cells were stained with crystal violet stain and visible plaques were counted. The percentage of plaque formation relative to the infected control (without iota-carrageenan treatment) was determined for each iota-carrageenan concentration.

Figure 1:
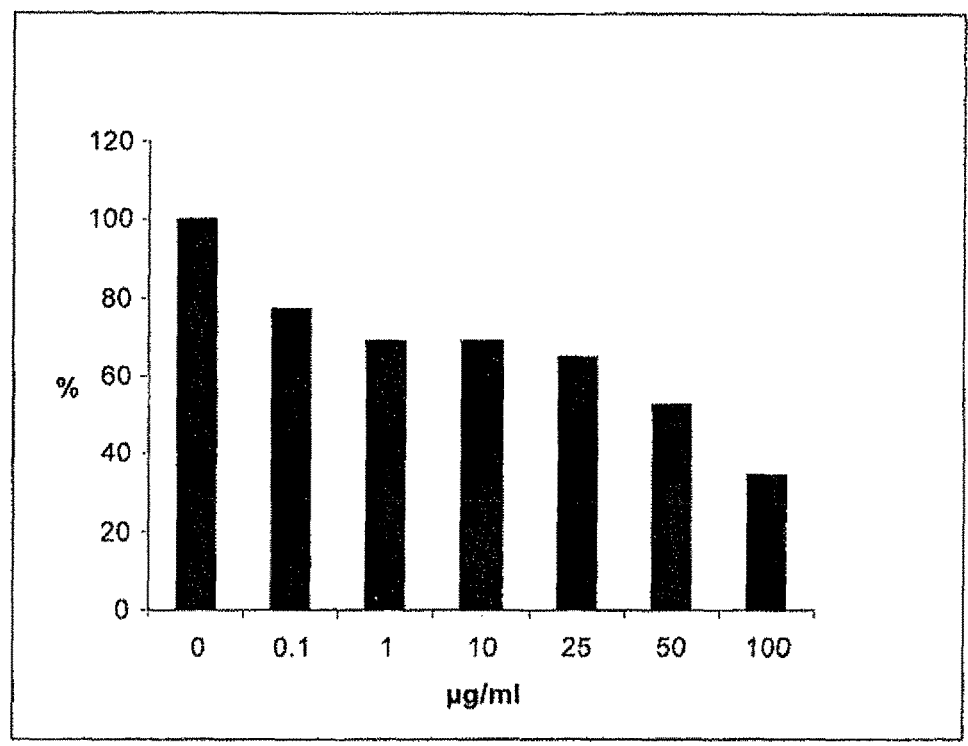
FIG. 1 shows the efficacy of iota-carrageenan in reducing plaque formation of influenza A/Chile/1/93 H1N1 virus in MDCK cells at different doses ranging from a final concentration of 0.1 to 100 µg/ml.

As shown in FIG. 1, it was found that iota-carrageenan inhibits, in a dose dependent manner, the plaque formation of influenza A/Chile/1/93 H1N1 virus in MDCK cells. A 50% reduction in plaque number (IC50) was achieved at a iota-carrageenan concentration of 50 μg/ml.

Example 2: Effect of Different Concentrations of Iota-Carrageenan on Influenza A Virus Plaque Formation in MDCK Cells Virus suspensions containing 60-80 pfu of influenza virus A/Aichi2/68 H3N2 were mixed with a iota-carrageenan stock solution to final concentrations of 75, 150 or 300 μg/ml. Confluent monolayers of the canine kidney cell line MDCK in six well plates were infected with the virus suspensions for 60 min at 34° C. The infection inoculum was removed and cells were washed with PBS and agarose overlay containing 0.6% agarose was added. Plates were incubated at 37° C. in a humidified atmosphere of 5% $CO_2$ in air. 48-60 h after infection the agarose overlay was removed, cells were stained with crystal violet stain and visible plaques were counted. The percentage of plaque formation relative to the infected control (without iota-carrageenan) was determined for each iota-carrageenan concentration.

As shown in FIG. 2, it was found that iota-carrageenan inhibits, in a dose dependent manner, the plaque formation of influenza A/Aichi/2/68 H3N2 virus in MDCK cells.

Example 3: Effect of Different Concentrations of Iota-Carrageenan on Parainfluenza Virus 3 Plaque Formation in Hep-2 Cells Virus suspensions containing 60-80 pfu of parainfluenza virus 3 were mixed with a iota-carrageenan stock solution to final concentrations of 0.1, 1, 10, 25, 50 and 100 µg/ml. The mixture was incubated for 1 h at 34° C.

Confluent monolayers of Hep-2 cells in six well plates were infected with the virus suspensions for 60 minutes a 34° C. The infection inoculum was removed and cells were washed with PBS and agarose overlay containing 0.6% agarose was added. The trays were incubated in a humidified, 5% $CO_2$ atmosphere. 48-60 h after infection the agraose overlay was removed, cells were stained with crystalviolett stain and visible plaques were counted. The percentage of plaque formation relative to the infected control (without iota-carrageenan) plates was determined for each iota-carrageenan concentration.

As shown in FIG. 3, it was found that iota-carrageenan inhibits, in a dose dependent manner, the plaque formation of parainfluenza virus 3 in Hep-2 cells. A 50% reduction in plaque number (IC50) was achieved at an iota-carrageenan concentration of 10 µg/ml.

Example 4: Effect of Preincubation with Iota-Carrageenan on Parainfluenza Virus 3 Plaque Formation in HeLa Cells Confluent monolayers of HeLa cells were incubated three hours with iota-carrageenan at a concentration of 13, 40, 133 and 400 µg/ml. The iota-carrageenan containing supernatant was removed and the cells were washed three times with PBS and thereafter infected with parainfluenza virus 3 as described in Example 3, but without addition of iota-carrageenan to the virus suspension. The percentage of plaque formation relative to the infected control (without iota-carrageenan pretreatment) was determined for each iota-carrageenan concentration.

As shown in FIG. 4, it was found that iota-carrageenan inhibits the plaque formation of parainfluenza virus 3 at a concentration of 400 and 133 µg/ml when cells were preincubated for three hours with iota-carrageenan, although no iota-carrageenan was present at the time of the infection and during the entire subsequent incubation period at 37° C. This result indicates that iota-carrageenan chemically or structurally modifies the surface receptors of the host cell in a way such that receptor-mediated binding of parainfluenza virus 3 to the host cell is hindered or prevented even in the absence of the modifying agent carrageenan. This is also proof of a strong prophylactic efficacy of iota-carrageenan.

Example 5: Effect of Eukaryotic Cell Pretreatment by Different Carrageenans on the Inhibition of Coronavirus Mediated Cell Death Subconfluent CK cells were infected in the presence of iota-, kappa- or lambda carrageenan at a concentration of 4, 40 and 400 µg/ml with feline coronavirus FIPV at a moi (multiplicity of infection) of 0.1) (see FIG. 5A). In comparison, subconfluent CK cells were incubated three hours with iota-, lambda or kappa-carrageenan at a concentration of 4, 40, and 400 µg/ml. The carrageenan containing supernatant was removed and the cells were washed three times with PBS and infected with feline coronavirus FIP (moi=0.1) in the absence of the polymer (see FIG. 5B). The percentage of viable cells relative to the uninfected control was determined for each carrageenan and each concentration.

As shown in FIG. 5A, all three types of carrageenan inhibit the coronavirus mediated cell death in CK cells at the highest concentration of 400 µg/ml. Iota-carrageenan still shows significant inhibition at a concentration of 4 µg/ml while kappa- and lambda-carrageenan are not effective at this concentration. From FIG. 5B it can be taken that in contrast to viruses that enter the cell via sugar receptors (see preceding examples), coronavirus infection does not seem to be inhibited due to a chemical or structural modification of the coronavirus-specific receptor(s) at the host cell surface by carrageenan, since it was not possible to increase host cell protection beyond a level of 35% inhibition even at the highest experimental carrageenan concentration of 400 µg/ml and at a preincubation period of three hours. Nor did the pretreatment of the host cells with carrageenan significantly improve cell protection against coronavirus infection. The results suggest that in order to achieve a significant protection against coronavirus infection the antiviral active agent, i.e. carrageenan, must be present at the time of infection, i.e. when an interaction between the virus and the host cell is about to occur.

Example 6: Effect of Eukaryotic Cell Pretreatment by Iota-Carrageenan on the Inhibition of HRV8 Mediated Cell Death Subconfluent HeLa cells were infected with human rhinovirus type 8 (HRV8, moi=0.1) in the presence of iota-carrageenan at concentrations of 4, 40 and 400 µg/ml (see FIG. 6A). In comparison, subconfluent HeLa cells were incubated for three hours with iota-carrageenan at a concentration of 4, 40 and 400 µg/ml prior to infection. The supernatant containing iota-carrageenan was removed and the cells were washed three times with PBS and then infected with HRV8 in the absence of the polymer (see FIG. 6B). The percentage of viable cells relative to the uninfected control was determined for each iota-carrageenan concentration.

As shown in FIG. 6A, iota-carrageenan inhibits the HRV8 mediated cell death at all concentrations. From FIG. 6B it can be taken that, in contrast to viruses that enter the cell via sugar receptors, HRV8 mediated cell death was not inhibited by more than 5% even at 400 µg/ml and where cells were preincubated for three hours with iota-carrageenan. This result is consistent with previous findings (data not shown) and suggests that for HRV8 the preincubation of the target cells with carrageenan does not significantly protect the target cells from becoming infected if carrageenan is missing at the time of infection. This result indicates that the receptor for HRV8, the LDL-receptor, is not modified or masked by the treatment with iota-carrageenan.

Example 7: Iota-Carrageenan is Quantitatively Removed from HeLa Cells by Washing the Cells with PBS Hela cells were incubated with FITC-labelled iota-carrageenan at a concentration of 400, 133, 4 and 0.4 µg/ml for 10 minutes, then the supernatant was removed and the cells were washed three times with PBS. The amount of residual FITC-labelled carrageenan was determined with a fluorescent detection reader (BMG-Omega) after removing the supernatant containing FITC-labelled iota-carrageenan and after each washing step. The fluorescent light units were converted into concentration values of µg/ml carrageenan by using a standard curve.

As shown in FIG. 7 FITC-labelled iota-carrageenan was quantitatively removed (>95%) from HeLa cells by washing the cells at least three times with PBS. This result proves that carrageenan does not covalently bind to the surface of the cells. The result was confirmed by a second experimental set, where the incubation period was extended from 10 minutes to 3 hours using the same detection method. The results thus support the conclusions drawn herein and in the examples concerned that carrageenan induces a modification of the sugar receptors on the target cell surface involved in the binding of the virions, which modification is still present after removal of the polymer from the target cell surface.

Example 8: Effect of Eukaryotic Cell Pretreatment by Iota-Carrageenan on the Inhibition of RSV Mediated Cell Death Subconfluent Vero cells were infected in the presence of iota-carrageenan at concentrations of 0.4, 4 and 40 µg/ml with RSV (moi=0.1). In comparison, subconfluent Vero cells were incubated for three hours with iota-carrageenan at a concentration of 0.4, 4 and 40 µg/ml. The iota-carrageenan containing supernatant was removed and the cells were washed three times with PBS and infected with RSV (moi=0.1) in the absence of the carrageenan. The percentage viable cells relative to the uninfected control was determined for each carrageenan concentration.

As shown in FIG. 8, iota-carrageenan inhibits the RSV mediated cell death at all concentrations even if the polymer is absent at the time of and during infection. It is known that RSV attaches to the cells via heparan sulphate, a sugar molecule that is present on the surface of epithelial cells. The results indicate that this receptor is modified by iota-carrageenan and the attachment of RSV to the cell surface and the subsequent viral replication is thereby blocked.

Example 9: Effect of Eukaryotic Cell Treatment with Iota-Carrageenan at Different Time Points After Infection on Inhibition of RSV Mediated Cell Death in HNep Cells Subconfluent HNep cells were infected with RSV (moi=0.1). Iota-carrageenan was added at a final concentration of 40 µg/ml at different time points post infection as indicated in FIG. 9 (0, 8, 24, 32, 48, 56 and 72 h post infection) and the percentage of viable HNep cells relative to the uninfected control was determined for each time point.

As shown in FIG. 9, iota-carrageenan significantly inhibits the RSV mediated cell death at a concentration of 100 µg/ml even when the polymer was added only 24 hours after infection. This result demonstrates that iota-carrageenan cannot only be used prophylactically but may also exert antiviral efficacy in the course of a therapeutic treatment when applied in the early phase of viral infection.

Example 10: Effect of Prophylactic Treatment with Iota-Carrageenan on Inhibition of RSV Mediated Cell Death in HNep Cells Subconfluent HNep cells were infected in the presence of iota-carrageenan at a concentration of 400, 133, 44, 15, 5, 2 and 1 µg/ml with RSV (moi=0.1). The percentage of viable HNep cells relative to an uninfected control was determined for each iota-carrageenan concentration.

As shown in FIG. 10, iota-carrageenan significantly inhibits the RSV mediated cell death even at a concentration as low as 1 µg/ml when the polymer was present during infection. This result demonstrates that iota-carrageenan can be used effectively for prophylactic intervention strategies.

Example 11: Effect of Eukaryotic Cell Treatment by Different Carrageenans on the Inhibition of RSV Mediated Cell Death in HEp-2 Cells HEp-2 cells in 6 well plates were infected in the presence of iota-, kappa- or lambda carrageenan at a concentration of 0.01, 0.1, 1, 10 and 100 µg/ml with RSV A2 virus (moi=0.001). The percentage of viable cells relative to the uninfected control was determined for each carrageenan and each concentration.

As shown in FIG. 11, all three types of carrageenan inhibit the RSV mediated cell death in HEp-2 cells with iota-carrageenan showing the strongest effect.

Example 12: Comparison of the Effect of Eukaryotic Cell Treatment by Iota-Carrageenan and Fucoidan on the Inhibition of RSV Mediated Cell Death Subconfluent HNep cells were infected in the presence of iota-carrageenan and fucoidan at a concentration of 400, 133, 44, 15, 4, 1.3 and 0.4 with RSV (moi=0.1). The percentage of viable HNep cells relative to an uninfected control was determined for each iota-carrageenan and each fucoidan concentration.

As shown in FIG. 12, fucoidan significantly inhibits the RSV mediated cell death in HNep cells at a concentration of 0.4 µg/ml when the polymer is present during infection. Fucoidan is therefore an interesting candidate for the development of products for prophylaxis and treatment of RSV infections.

Example 13: Effect of Eukaryotic Cell Treatment with Different Carrageenans and Fucoidan on the Inhibition of Parainfluenza Virus 3 Mediated Cell Death Subconfluent HNep cells were infected in the presence of either iota-, kappa-, lambda-carrageenan or fucoidan at a concentration of 400, 133.3, 44.4, 14.8, 4, 1.3 and 0.4 µg/ml with parainfluenza virus type 3. The percentage of viable (hence uninfected) HNep cells relative to the uninfected control was determined for each polymer and each polymer concentration.

As shown in FIG. 13, all three types of carrageenan inhibit the parainfluenza virus 3 mediated cell death in HNep cells with iota-carrageenan showing the strongest effect. Fucoidan also inhibits the parainfluenza virus 3 mediated cell death in HNep cells at an extent comparable to the inhibitory effect of kappa- and lambda-carrageenan.

Example 14: Effect of Eukaryotic Cell Treatment with Different Carrageenans and Fucoidan on the Inhibition of Influenza Virus H3N2 Mediated Cell Death Subconfluent HNep cells were infected in the presence of iota-, kappa-, lambda-carrageenan and fucoidan at a concentration of 400, 133.3, 44.4, 14.8, 4, 1.3 and 0.4 µg/ml with influenza virus H3N2. The percentage of viable HNep cells relative to the uninfected control was determined for each polymer and each polymer concentration.

As shown in FIG. 14, all three types of carrageenan inhibit the influenza virus H3N2 mediated cell death in HNep cells. In addition, it was found that fucoidan inhibits the influenza virus H3N2 mediated cell death in HNep at an extent comparable to that of iota-carrageenan.

Example 15: Effect of Different Carrageenans and Fucoidan on Avian Influenza Virus H5N1 Plaque Formation in MDCK Cells Virus suspensions containing 60-80 pfu of avian influenza virus H5N1 were mixed with a polymer stock solution of either iota-, kappa-, lambda-carrageenan or fucoidan to final polymer concentrations of 400 or 44.4 µg/ml. Confluent monolayers of the canine kidney cell line MDCK in six well plates were infected with the virus suspensions for 60 min at 34° C. The infection inoculum was removed and cells were washed with PBS and agarose overlay containing 0.6% agarose was added. Plates were incubated at 36° C. in a humidified atmosphere of 5% $CO_2$ in air. 48-60 h after infection the agarose overlay was removed, cells were stained with crystal violet stain and visible plaques were counted. The percentage of plaque formation relative to the infected control (without polymer treatment) was determined for each polymer and each polymer concentration.

As shown in FIG. 15, it was found that plaque formation of avian influenza virus H5N1 was not influenced by iota- and lambda carrageenan and fucoidan. However, kappa-carrageenan inhibits, in a dose dependent manner, the plaque formation of avian influenza virus H5N1 in MDCK cells. Since avian influenza virus preferably binds to sialic acid residues with alpha 2-3 linkage the results indicate that kappa-carrageenan may preferably modify such sialic acid residues having 2-3 linkage.

Example 16: Effect of Prophylactic Eukaryotic Cell Treatment with Iota-Carrageenan on the Inhibition of Adenovirus Type B (Ad50) Mediated Cell Death Subconfluent HNep cells were infected in the presence of iota-carrageenan at a concentration of 400, 133.3, 44.4, 14.8, 4, 1.3 and 0.4 µg/ml with Ad50. The percentage of viable HNep cells relative to the uninfected control was determined for each iota-carrageenan concentration.

As shown in FIG. 16, iota-carrageenan significantly inhibits the Ad50 mediated cell death even at a concentration as low as 4 µg/ml when the polymer is present at the time of and during infection. This result is an indication that iota-carrageenan may be used for effective prophylactic intervention strategies against adenovirus of the subtype B (e.g. Ad50). However, when other adenoviruses from subtypes A, C and D were tested in an experimental set as described above no significant effect of iota-carrageenan was detected (data not shown).

Example 17: Comparison of the Effect of Prophylactic Eukaryotic Cell Treatment with Iota-Carrageenan on the Inhibition of Ad50 Mediated Cell Death Subconfluent HNep cells were infected in the presence of iota-carrageenan at a concentration of 400, 40 and 4 µg/ml with Ad50. In comparison, subconfluent HNep cells were incubated for three hours with iota-carrageenan at a concentration of 400, 40 and 4 µg/ml prior to infection. The supernatant containing iota-carrageenan was removed and the cells were washed three times with PBS and infected with Ad50 in the absence of the carrageenan. The percentage of viable HNep cells relative to the uninfected control was determined for each iota-carrageenan concentration.

As shown in FIG. 17, iota-carrageenan significantly inhibits the Ad50 mediated cell death at a concentration of 400 and 40 µg/ml in the presence and in the absence of iota-carrageenan at the time of infection and during the observed infection period. These data indicate that iota-carrageenan modifies the cell surface receptor for adenoviruses from subtype B, which is known to be a sugar receptor, while adenoviruses from other subtypes probably enter the cell via different receptors.

What is claimed is:

1. A method of treating a subject having an upper respiratory tract infection caused by a virus selected from the group consisting of paramyxovirus, human influenza A virus, and adenovirus of subtype B, comprising administering to the subject a pharmaceutical composition comprising a carrageenan component as the sole antiviral active ingredient in an antiviral effective amount, wherein in the administering, the carrageenan component is the sole antiviral active ingredient administered,
wherein:
the carrageenan component comprises iota-carrageenan, or kappa-carrageenan, or a combination of iota- and kappa-carrageenan, or salts thereof in an amount of 80% by weight or more relative to the total dry weight of all carrageenans or salts thereof present in the composition;
the pharmaceutical composition does not contain a surfactant;
the pharmaceutical composition is administered topically on skin or mucosa; and
the active antiviral ingredient is effective in treating the upper respiratory tract infection by either:
a) specifically interfering with at least one viral action selected from the group consisting of virus penetration of eukaryotic cells, virus replication in eukaryotic cells, virus assembly, and virus release from infected eukaryotic cells, or
b) unspecifically inhibiting a virus titer increase or unspecifically reducing a virus titer level in a eukaryotic or mammalian host system.

2. The method according to claim 1, wherein the virus is a virus that enters a host cell via receptor-mediated attachment to the cell, the receptor comprising one or more sugar residues.

3. The method according to claim 1, wherein said virus is a paramyxovirus.

4. The method according to claim 1, wherein said virus is a human influenza A virus.

5. The method according to claim 4, wherein said virus binds to the host cell via a cell surface receptor that comprises sialic acid residues having alpha 2-6 linkages.

6. The method according to claim 1, wherein said virus is an adenovirus of subtype B.

7. The method according to claim 3, wherein said paramyxovirus is selected from the group consisting of human parainfluenza virus (HPV) type 1, HPV type 2, HPV type 3, HPV type 4 and RSV.

8. The method according to claim 7, wherein said paramyxovirus is RSV.

9. The method according to claim 1, wherein the antiviral pharmaceutical composition is administered topically on skin or mucosa in the form of one of a skin lotion, cream, ointment, gel, powder, spray, foam, liquid drops, or a gargle solution.

10. The method according to claim 9, wherein the composition is liquid or semi-solid and comprises as a ready-for-use preparation iota-carrageenan in an amount of between 0.01% and 10% by weight, relative to the total volume of the preparation.

11. The method according to claim 1, wherein the composition comprises kappa-carrageenan.

12. The method according to claim 1, wherein the carrageenan component in the combination of iota- and kappa-carrageenan and the combination comprises 50% or more by dry weight of iota-carrageenan, relative to the total dry weight of carrageenans present in the composition.

13. The method according to claim 1, wherein said composition further comprises at least one pharmaceutically acceptable carrier and/or additive.

14. The method according to claim 13, wherein the pharmaceutically acceptable additive comprises a pharmaceutically acceptable alkali metal salt.

15. The method according to claim 14, wherein said pharmaceutically acceptable salt is present in the composition in an amount of 1% or less.

16. The method according to claim 1, wherein the composition comprises a part or all of the carrageenan component by way of its salt.

17. The method according to claim 1, wherein the composition is sterile.

18. The method according to claim 1, wherein prior to the administering the composition is coated or impregnated onto a solid surface of a hygiene or sanitary item and the administering comprises the subject contacting the coated or impregnated surface of the hygiene or sanitary item.

19. The method according to claim 1, wherein prior to the administering the composition is integrated in a lipstick and the administering comprises the subject contacting the lipstick.

20. The method according to claim 1, wherein the subject is an individual being a high-risk patient selected from the group consisting of a COPD-patient, an asthma patient, a person with allergies, a person with impaired immune, cardiac, or pulmonary system, and a transplantation patient.

21. The method according to claim 18, wherein the sanitary item is a hygiene or sanitary glove, tissue or paper, a nasal tissue or paper, a cotton swab, dust mask or sanitary or medical facial mask.

22. The method of claim 9, wherein the powder is adapted for inhalation.

23. The method according to claim 1, wherein the composition does not contain a silicate.

24. A method of treating a subject having an upper respiratory tract infection caused by a virus selected from the group consisting of paramyxovirus, human influenza A virus, and adenovirus of subtype B, the method consisting essentially of administering to the subject a pharmaceutical composition comprising a carrageenan component as the sole antiviral active ingredient in an antiviral effective amount, wherein in the administering, the carrageenan component is the sole antiviral active ingredient administered, wherein:
  the carrageenan component comprises iota-carrageenan, or kappa-carrageenan, or a combination of iota- and kappa-carrageenan, in an amount of 80% by weight or more relative to the total dry weight of all carrageenans present in the composition;
  the pharmaceutical composition does not contain a surfactant;
  the pharmaceutical composition is administered topically on skin or mucosa; and
  the active antiviral ingredient is effective in treating the upper respiratory tract infection by either:
    a) specifically interfering with at least one viral action selected from the group consisting of virus penetration of eukaryotic cells, virus replication in eukaryotic cells, virus assembly, and virus release from infected eukaryotic cells, or
    b) unspecifically inhibiting a virus titer increase or unspecifically reducing a virus titer level in a eukaryotic or mammalian host system.

25. The method of treatment recited in claim 24, the method consisting of administering to the subject a pharmaceutical composition comprising a carrageenan component as the sole antiviral active ingredient in an antiviral effective amount.

26. The method of claim 9, wherein the antiviral pharmaceutical composition is administered in the form of a nose spray.

* * * * *